(12) United States Patent
Jenison et al.

(10) Patent No.: US 10,675,473 B2
(45) Date of Patent: Jun. 9, 2020

(54) IMPLANTABLE MEDICAL DEVICE COILS

(71) Applicant: Medtronic, Inc., Minneapolis, MN (US)

(72) Inventors: Troy A. Jenison, Minneapolis, MN (US); Andrew J. Ries, Lino Lakes, MN (US); Kent E. Samuelson, Parker, CO (US)

(73) Assignee: Medtronic, Inc., Minneapolis, MN (US)

( * ) Notice: Subject to any disclaimer, the term of this patent is extended or adjusted under 35 U.S.C. 154(b) by 158 days.

(21) Appl. No.: 15/868,358

(22) Filed: Jan. 11, 2018

(65) Prior Publication Data

US 2019/0209848 A1    Jul. 11, 2019

(51) Int. Cl.
| | | |
|---|---|---|
| A61N 1/372 | (2006.01) | |
| A61N 1/378 | (2006.01) | |
| A61N 1/36  | (2006.01) | |
| A61N 1/05  | (2006.01) | |
| A61N 1/375 | (2006.01) | |
| A61N 1/08  | (2006.01) | |

(52) U.S. Cl.
CPC ....... *A61N 1/37229* (2013.01); *A61N 1/0534* (2013.01); *A61N 1/36062* (2017.08); *A61N 1/36125* (2013.01); *A61N 1/3787* (2013.01); *A61N 1/37247* (2013.01); *A61N 1/086* (2017.08); *A61N 1/37211* (2013.01); *A61N 1/37514* (2017.08)

(58) Field of Classification Search
USPC ..................................... 607/36, 60
See application file for complete search history.

(56) References Cited

U.S. PATENT DOCUMENTS

| | | | |
|---|---|---|---|
| 4,542,532 A      | 9/1985  | McQuilkin | |
| 6,298,271 B1     | 10/2001 | Weijand et al. | |
| 6,463,329 B1     | 10/2002 | Goedeke | |
| 6,944,489 B2     | 9/2005  | Zeijlemaker et al. | |
| 8,428,744 B2     | 4/2013  | Stancer et al. | |
| 8,666,512 B2     | 3/2014  | Walker et al. | |
| 9,042,997 B2     | 5/2015  | Rahman et al. | |
| 9,067,072 B2     | 6/2015  | Tahmasian et al. | |
| 9,669,208 B2     | 6/2017  | Harberts et al. | |
| 2011/0054270 A1* | 3/2011  | Derchak | A61B 5/0002 600/300 |
| 2011/0190852 A1* | 8/2011  | Dinsmoor | A61B 5/0031 607/60 |

* cited by examiner

*Primary Examiner* — Nicole F Lavert
*Assistant Examiner* — Nicole F Johnson
(74) *Attorney, Agent, or Firm* — Shumaker & Sieffert, P.A.

(57) ABSTRACT

An implantable medical device (IMD) may include a plurality of coils that may be used to recharge a power supply of the IMD and/or provide telemetry for the IMD. The IMD may be configured to couple all of the coils in series, such that currents that are induced by each of the coils are added together when the IMD is exposed to an electromagnetic field. The IMD may be configured to alter the coupling of the coils such that the coils are coupled in series opposition, such that currents that are induced by some coils of the IMD are opposed by currents that are induced by other coils of the IMD.

23 Claims, 10 Drawing Sheets

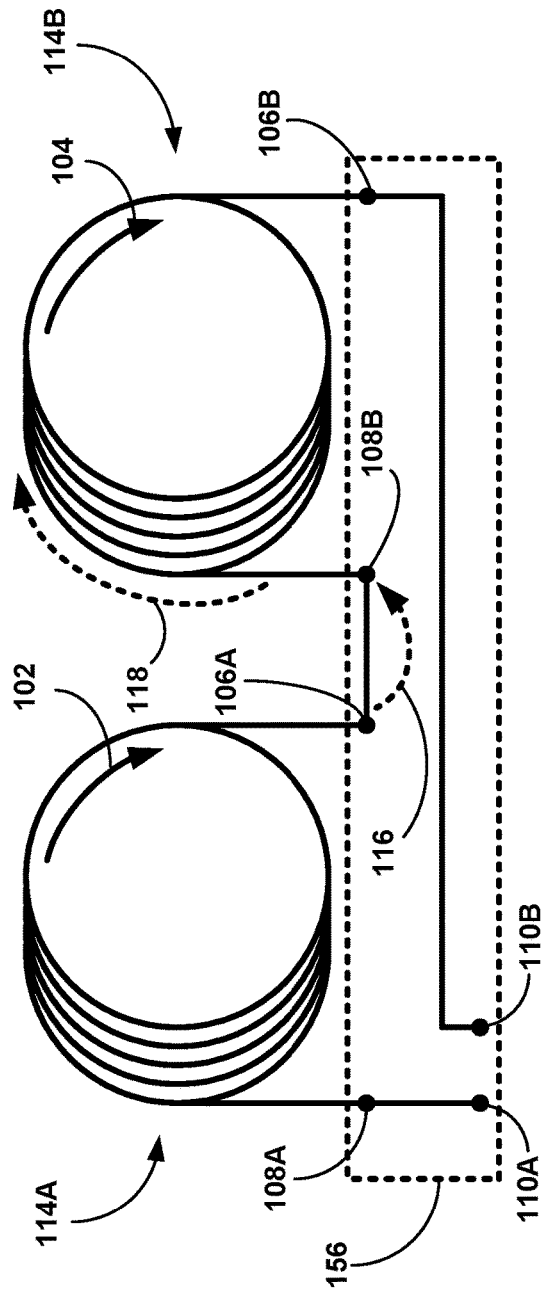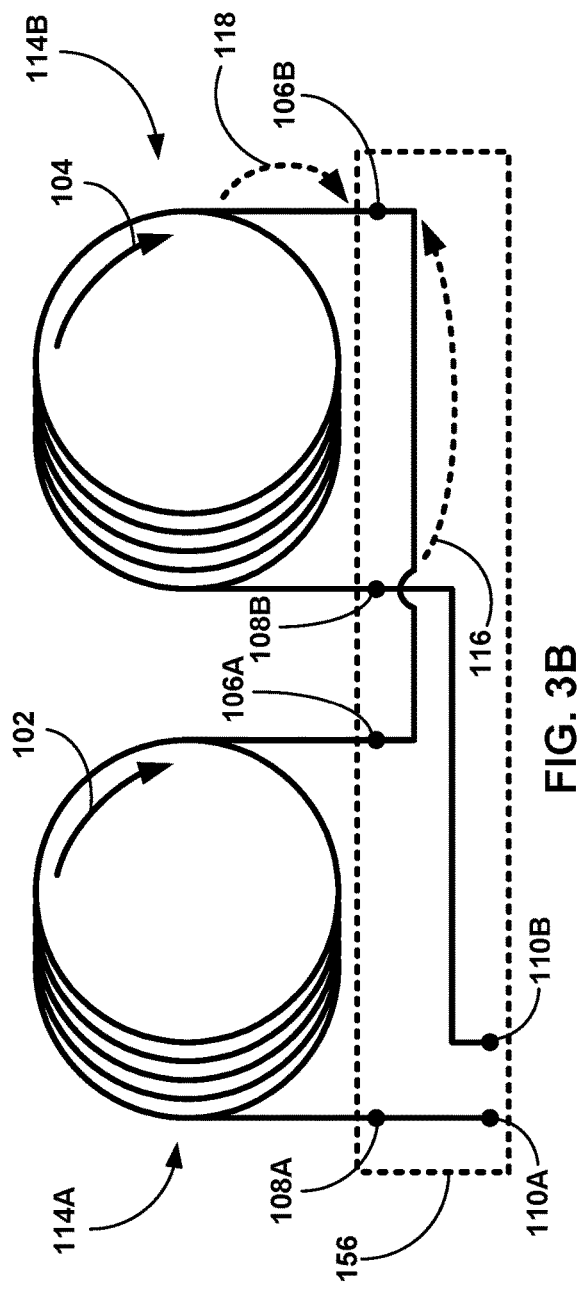

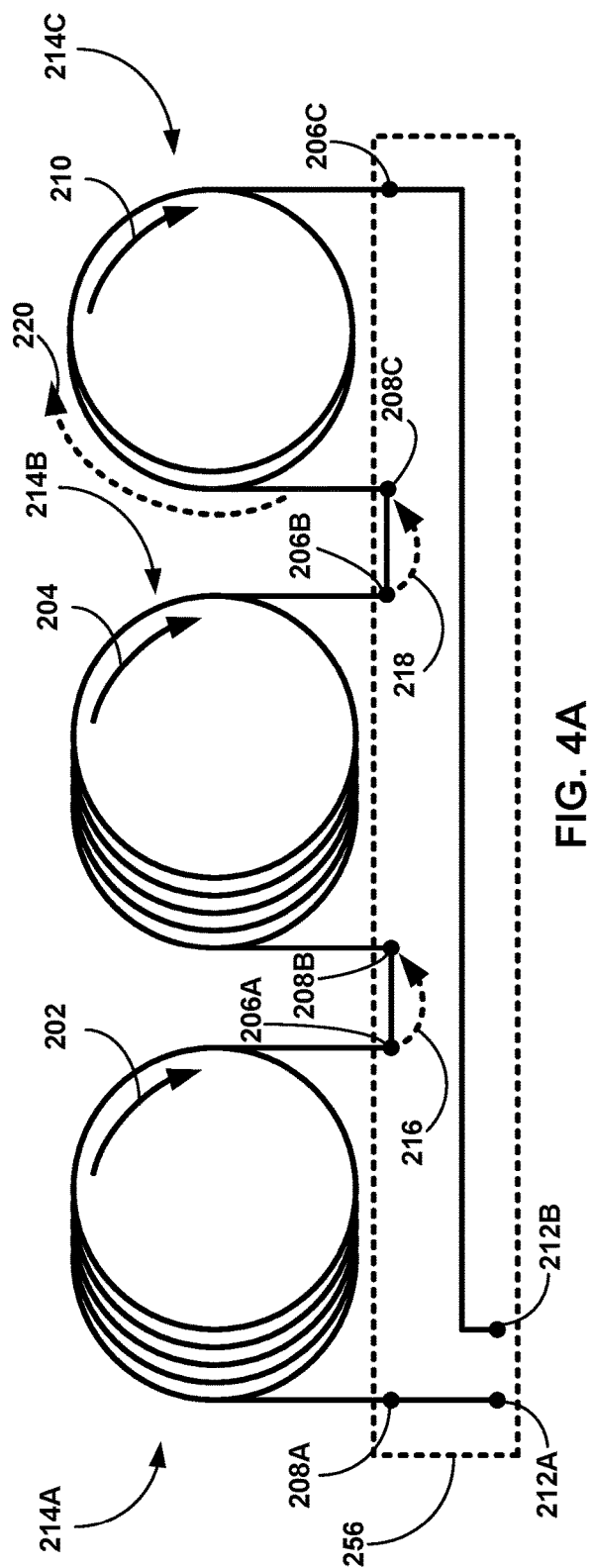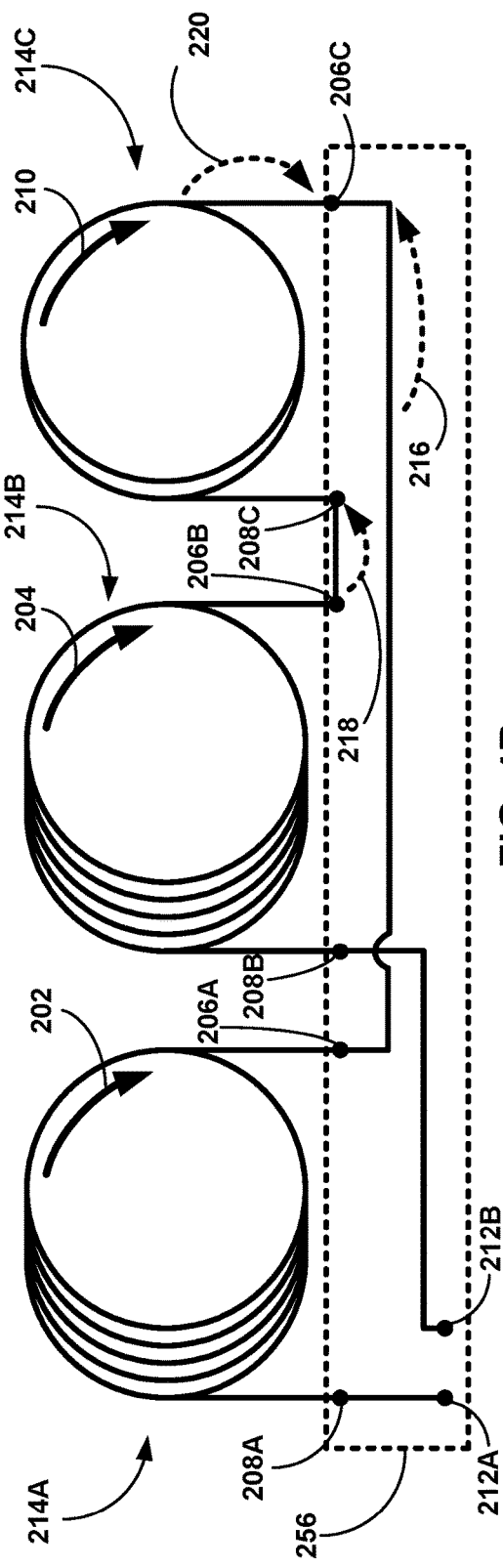

IMPLANTABLE MEDICAL DEVICE COILS

TECHNICAL FIELD

The disclosure relates to coils for use with implantable medical devices, e.g., for wireless communication or charging.

BACKGROUND

Medical devices may be external or implanted. Implantable medical devices (IMDs) may serve a wide variety of functions, such as sensing one or more parameters of a patient, delivering one or more therapies to the patient, or a combination of these and other functions. An IMD may deliver therapy to, and/or monitor a physiological condition of, a variety of organs, nerves, muscles, tissues or vasculatures of the patient, such as the heart, brain, stomach, spinal cord, pelvic floor, or the like. The therapy provided by the IMD may include electrical stimulation therapy, drug delivery therapy or the like.

The IMD may include a power source such as a battery. The power source may be configured to provide power for the IMD to execute the functions for which the IMD was designed. In some examples, the power source may be rechargeable. The power source may be rechargeable through the use of coils that are configured to induce a current that is then channeled into the power source.

The IMD may also transmit communications to and/or receive communications from another device via wireless telemetry. The IMD may transmit and/or receive communications with another device that is implanted, attached to (e.g., worn by) the patient or otherwise located near the patient, or remote from the patient. The communications may include information related to a condition of the patient, such as physiological signals measured by one or more sensors, information related to a therapy delivered to the patient, or information that may be used to control or configure a therapy to be delivered to the patient or physiological signal measurement. The IMD may transmit and/or receive information using any of a variety of wireless communication techniques, including inductive telemetry, magnetic telemetry, radio frequency (RF) telemetry, or the like.

SUMMARY

Aspects of the disclosure are directed to coils of the implantable medical device (IMD) that are used to, for example, recharge a battery or other power source of the IMD and/or provide telemetry for the IMD. The coils may be configured to transmit or receive signals for the IMD, e.g., induce a current that may then be channeled into a power source of the IMD. The IMD may be configured to electrically couple all of the coils in series, such that currents that are induced by each of the coils are additive in relation to each other when the IMD is exposed to an electromagnetic field. The IMD may be further configured to electrically couple the coils in series opposition, such that currents that are induced by some of the coils of the IMD are opposed by currents that are induced by other of the coils of the IMD, such that a current that is induced by the coils of the IMB is at least partially cancelled. A switch of the IMD may alter a coupling of the coils from series to series opposition in response to determining that the coils are inducing more current than desired, such that the IMD is overheating or is otherwise inducing undesirably high voltages (e.g., that may overcharge a respective battery). In this way, the IMD may be configured to use coils that may recharge a battery or provide telemetry for the IMB while also being configured to be exposed to the relatively intense electromagnetic fields of various electromagnetic interference (EMI) sources, such as magnetic reasoning imagining (MRI) machines, without inducing an amount of current or voltage that may cause adverse effects to the IMB or the patient.

In other examples, aspects of the disclosure relate to an implantable medical device that includes an implantable medical housing, a processing circuit within the implantable medical housing, a first coil that is configured to wirelessly receive a signal and is secured to the implantable medical device, a second coil that is configured to wirelessly receive the signal and is secured to the implantable medical device, switching circuitry within the housing, and a sensor. The processing circuit may be configured to cause the switching circuitry to selectably couple the first coil to the second coil in either series, such that the first coil is coiled in a same direction as the second coil, or in series opposition, such that the first coil is coiled in the opposite direction as the second coil. The sensors sense a parameter that indicates a magnitude of an induced current that is induced over the first coil and the second coil as a result of receiving the signal. The parameter is at least one of temperature, voltage, or current.

In other examples, aspects of the disclosure relate to a method of managing coils of an implantable medical device. The method includes coupling by a switching circuit, as caused by a processing circuit of the implantable medical device, a first coil that is secured to the implantable medical device to a second coil that is secured to the implantable medical device in series such that the first coil is coiled in a same direction as the second coil, wherein both the first coil and the second coil are configured to wirelessly receive a signal. The method further includes receiving, by both the first coil and the second coil, the signal. The method further includes detecting, by the processing circuit, that a parameter that indicates a magnitude of an induced current that is induced over the first coil and the second coil as a result of receiving the signal surpasses a predetermined threshold. The method further includes coupling, by switching circuitry of the implantable medical device as caused by the processing circuit, the first coil and second coil in series opposition such that the first coil is coiled in the opposite direction as the second coil.

In other examples, aspects of the disclosure relate to an implantable medical device comprising an implantable medical housing, a processing circuit within the implantable medical housing, one or more leads that are configured to extend from the implantable medical housing and be implanted into a brain of a patient, one or more electrodes at a distal end of the one or more leads that are configured to deliver electrical stimulation to the brain of the patient, a stimulation circuit configured to generate the electrical stimulation, a power supply that is configured to provide power for the generation of the electrical stimulation, switching circuitry that is electrically coupled to the processing circuit, a first coil that is coupled through the switching circuitry to the power supply and configured to wirelessly receive a charging signal, a second coil that is coupled through the switching circuitry to the power supply and configured to wirelessly receive the signal, and a sensor. The processing circuit is configured to cause the switching circuitry to selectably couple the first coil to the second coil in either series such that the first coil is coiled in a same direction as the second coil or in series opposition such that the first coil is coiled in an opposite direction as the second coil. The sensor senses a parameter that indicates a magnitude of an induced current that is induced over the first coil and the second coil as a result of receiving the signal. The parameter is at least one of temperature, voltage, or current.

The details of one or more example are set forth in the accompanying drawings and the description below. Other features, objects, and advantages will be apparent from the description and drawings, and from the claims.

BRIEF DESCRIPTION OF DRAWINGS

FIGS. 3A and 3B are conceptual and schematic diagrams of two coils of an IMD being coupled in series and series opposition, respectively.

FIGS. 4A and 4B are conceptual and schematic diagrams of three coils of an IMD being coupled in series and series opposition, respectively.

DETAILED DESCRIPTION

This disclosure is generally directed to coils of an implantable medical device (IMD) that is used to monitor a parameter of a patient and/or deliver a therapy to a patient. The IMB may include two or more coils. The coils may be used to recharge a battery or power source of the IMD, or otherwise to receive power from an external power source (e.g., through inductive coupling). Alternatively, and/or additionally, the coils may be used as an antenna to transmit or receive wireless communication signals. The IMB may be include a switch (hereinafter referred to as "switching circuitry") that alters the manner in which the coils are electrically coupled to components of the IMD. For example, the IMB may include two substantially similar coils that the switching circuitry may electrically couple in series. When coupled in series, the two substantially similar coils may each induce substantially similar currents that are then combined and channeled into a power source of the IMB. The switching circuitry may also electrically couple the two coils in series opposition, such that the two substantially similar coils may induce substantially opposite currents that, in some examples, effectively cancel each other.

Figure 1A:
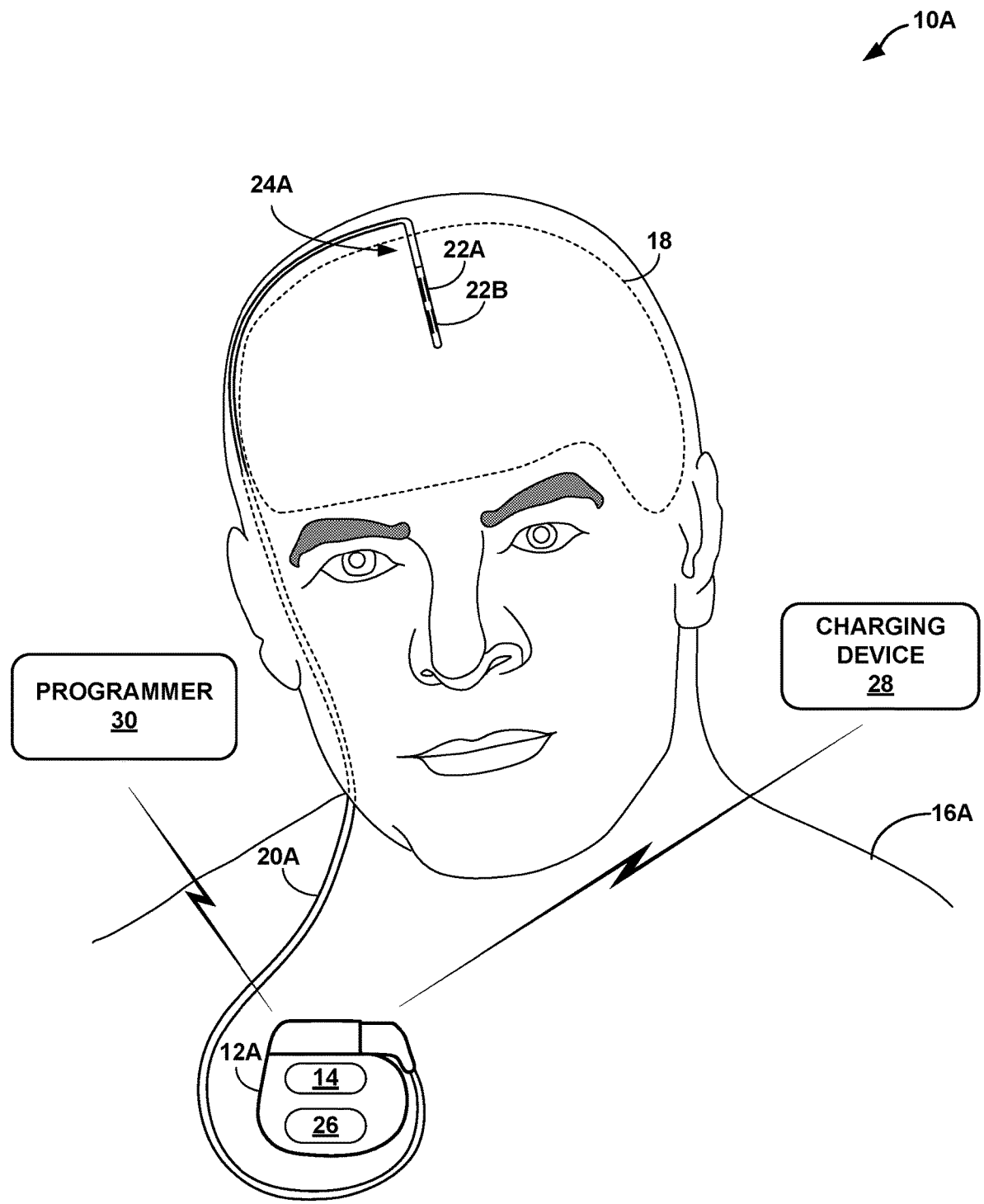
FIG. 1A is a conceptual and schematic diagram illustrating an example system that includes an implantable medical device (IMD) and a lead implanted into a brain of a patient.
Figure 1B:
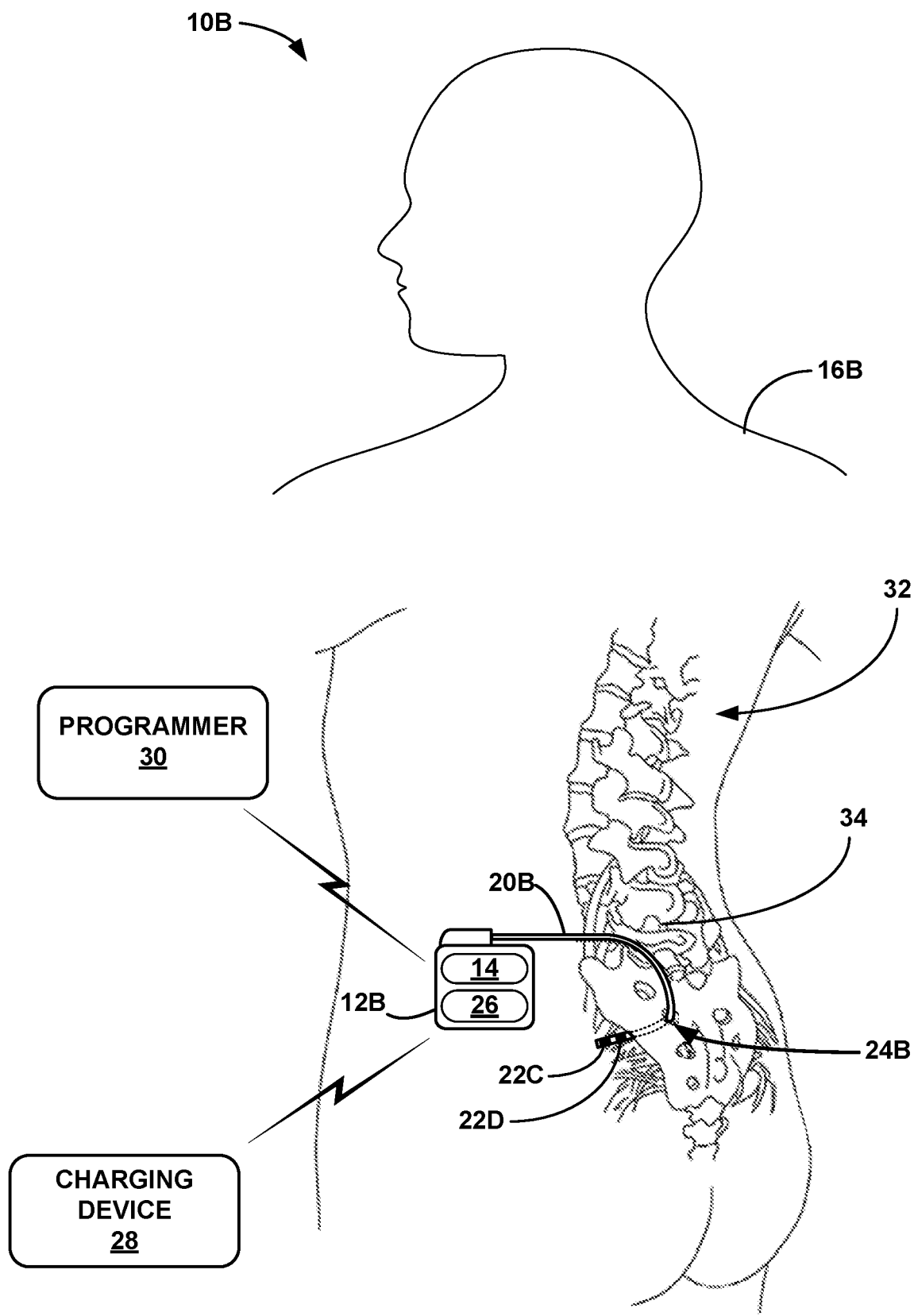
FIG. 1B is a conceptual and schematic diagram illustrating an example system that includes an implantable medical device (IMD) and a lead implanted near a spinal cord of a patient.

FIGS. 1A and 1B are conceptual diagrams illustrating example systems 10A and 10B (collectively "systems 10") that includes implantable medical devices 12A and 12B (collectively "IMDs 12"), each of which includes with internal coils 14. IMDs 12 are depicted as implanted in patients 16A and 16B (collectively "patients 16"). IMDs 12 may deliver therapy and/or monitor patients 16 using electrodes 22A, 22B, 22C, 22D (collectively "electrodes 22").

For example, in FIG. 1A, medical system 10A includes an IMB 12A configured to deliver therapy to and/or sensing physiological signals from brain 18 of patient 16A through lead 20A. Specifically, IMD 12A includes lead 20A entering through a cranium of patient 16A and implanted within brain 18 of patient 16A to deliver deep brain stimulation (DBS). One or more electrodes 22A, 22B at distal end 24A of lead 20A provide electrical pulses to surrounding anatomical regions of brain 18 in a therapy that may alleviate a condition of patient 16A. In some examples, more than one lead 20A may be implanted within brain 18 of patient 16A to stimulate multiple anatomical regions of the brain.

DBS may be used to treat dysfunctional neuronal activity in the brain which manifests as diseases or disorders such as Huntington's Disease, Parkinson's Disease, or movement disorders. The exact reasons why electrical stimulation therapy is capable of treating such conditions of the brain is unknown, but symptoms of these diseases can be lessened or eliminated with electrical stimulation therapy. Certain anatomical regions of brain 18 are responsible for producing the symptoms of such brain disorders. As one example, stimulating an anatomical region, such as the Substantia Nigra, in brain 18 may reduce the number and magnitude of tremors experienced by patient 16A. Other anatomical regions may include the subthalamic nucleus, globus pallidus interna, ventral intermediate, and zona inserta. Anatomical regions such as these are targeted by the clinician during the implantation of lead 20A. In other words, the clinician may attempt to position the distal portion of lead 20A, including electrodes 22A, 22B, as close to these regions as possible.

IMD 12A may include two or more internal coils 14 that are configured to create or cancel one or more induced currents as a result of electromagnetic fields. For example, IMD 12A may include power source 26 that is configured to produce power for IMD 12A to deliver electrical stimulation and/or detect electrical signals, and recharge coils 14 may be coupled in series by IMD 12A to recharge power source 26 in response to an electromagnetic field created by charging device 28, e.g., when coils 14 act as recharge coils. In some examples, IMD 12A may be configured to transmit signals to or receive signals from programmer 30, e.g., when coils 14 act as telemetry coils when coils 14 are coupled in series.

Further, in either or both cases, IMD 12A may be configured to modify a coupling of coils 14 such that some of coils 14 are electrically coupled in series opposition in relation to others of coils 14, therein cancelling a total induced current of coils 14. For example, IMD 12A may couple coils 14 in series opposition when patient 16A undergoes magnetic-resonance imaging (MRI) testing, to reduce or eliminate a chance of a relatively high current being induced by coils 14 of IMD 12A. By configuring IMD 12A to have a capability to couple coils 14 in series opposition, IMD 12A may have an increased ability to regulate a temperature of IMD 12A and/or the tissue of patient 16A surrounding IMD 12A. Though depicted as separate components for the sake of illustration, in other examples the functions provided by charging device 28 and programmer 30 may be provided partially or entirely by a single component. Additionally, it is to be understood that the depicted location of coils 14 and power source 26 within IMD 12A is for purposes of illustration only, as coils 14 and power source 26 may be located within or about IMD 12A at many locations in many orientations.

In the example of FIG. 1B, system 10B includes IMD 12B that may be configured to deliver therapy to and/or sense physiological signals from target tissue. The target tissue may include or be near spinal cord 32 and/or pelvic nerves 34 (e.g., a pudendal nerve or sacral nerve), or any other nervous or muscle tissue that may be stimulated or from which physiological signals of patient 16B may be sensed through lead 20B. More particularly, IMD 12B may deliver electrical stimulation and sense electrical signals via electrodes 22C, 22D at distal end 24B of lead 20B. IMD 12B may provide stimulation to treat symptoms of patient 16B, such as pain, fecal or urinary incontinence, erectile dysfunction, or other sexual dysfunction.

IMDs 12 may include electronics and other internal components necessary or desirable for providing the functionality described herein as being associated with the device. In one example, IMDs 12 include processing circuitry, memory, signal generation circuitry, sensing circuitry, and a telemetry circuitry. In general, memory of IMD 12 may include computer-readable instructions that, when executed by a processing circuit of the IMD, cause it to perform various functions attributed to the device herein. For example, the processing circuit of an IMD 12 may control the signal generation circuitry and sensing circuitry according to instructions and/or data stored on memory to deliver therapy to patient 16, sense physiological signals of patient 16, and perform other functions related to treating one or more conditions of patient 16 with IMD 12.

The signal generation circuitry of IMD 12 may generate electrical stimulation that is delivered to patient 16 via electrodes 22 on one or more leads 20, in order to provide, for example, DBS, spinal cord stimulation, or other neuromodulation (e.g., neurostimulation). The sensing circuitry of IMD 12 may monitor electrical signals from electrodes on leads 20 of IMD 12 in order to monitor electrical activity of the patient, e.g., to monitor electrical signals generated by brain 18, or other neurological signals or action potentials. Telemetry circuitry of IMD 12 may include any suitable hardware, firmware, software or any combination thereof for communicating with another device, such as programmer 30. Under the control of a processing circuit of IMD 12, the telemetry circuitry may use coils 14 to receive downlink telemetry from and send uplink telemetry to programmer 30.

Programmer 30 may be a handheld computing device, computer workstation, or networked computing device. Programmer 30 may include electronics and other internal components necessary or desirable for executing the functions associated with the device. In one example, programmer 30 includes one or more processing circuits and memory, as well as a user interface, telemetry circuitry, and power source.

In other examples, IMD 12 may be used for other forms of treatment or monitoring. For example, IMD 12 may be implanted near a heart of patient 16 and be used to provide therapy to the heart or monitor a parameter of the heart. In this example, IMD 12 may be configured provide defibrillation therapy to the heart or otherwise provide electric signals to or read electrical signals from the heart. Other examples of IMD 12 being implanted in different areas of patient 16 to provide therapy to or monitor different areas of patient 16 are also possible.

Figure 2:
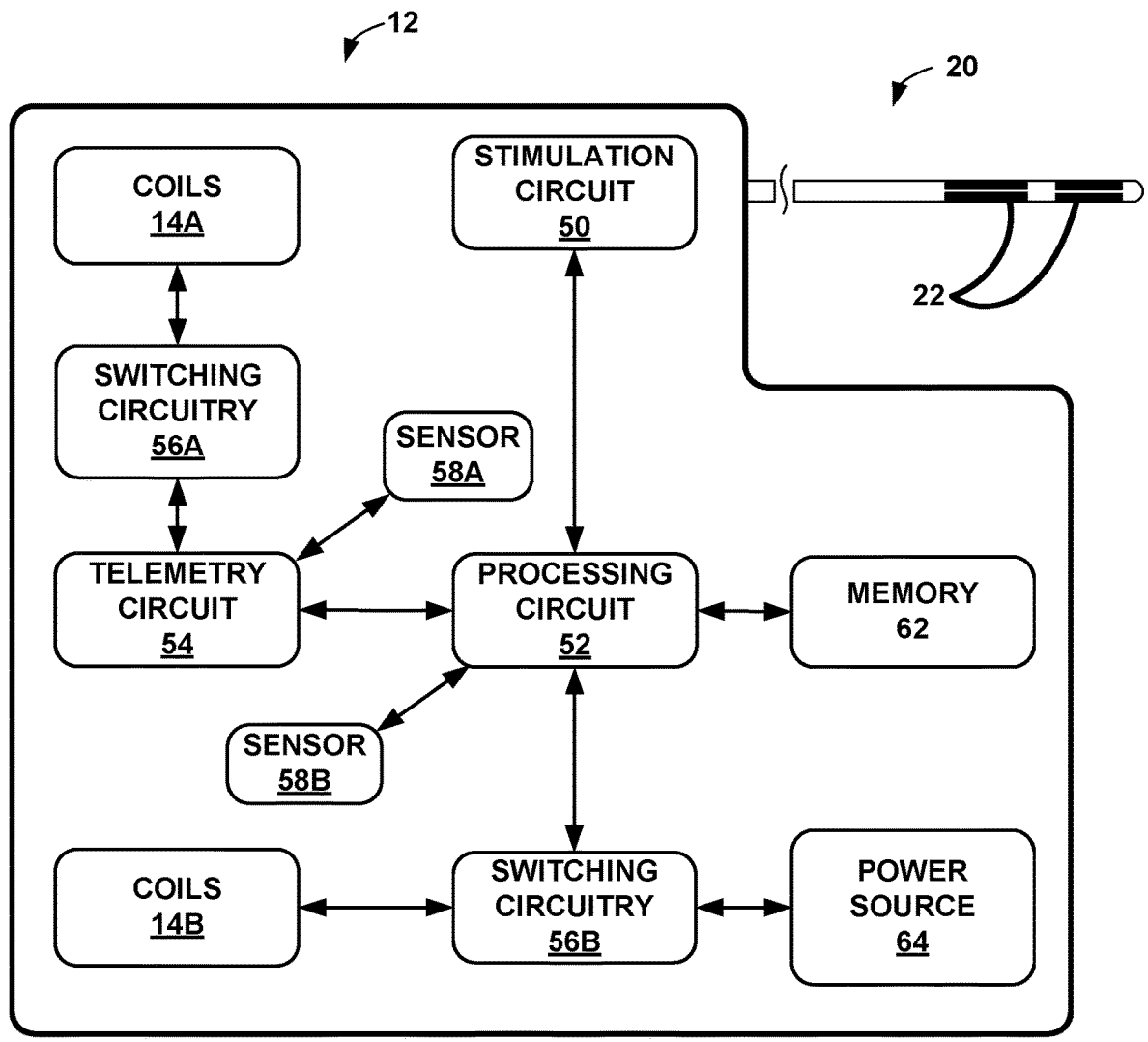
FIG. 2 is a conceptual and schematic block diagram of the IMD of FIGS. 1A and 1B.

FIG. 2 is a block diagram illustrating example components of IMD 12. In the example of FIG. 2, IMD 12 includes stimulation circuit 50, processing circuit 52, telemetry circuit 54, switching circuitry 56A and 56B, sensor 58A and 58B (collectively "sensors 58"), coils 14A and 14B (collectively "coils 14"), memory 62, and power source 64. In other examples, IMD 12 may include a greater or fewer number of components. In some examples, IMD 12 may not include coils 14B, switching circuitry 56B, or sensor 58B, and may instead use coils 14A (and related switching circuitry 56A and sensor 58A) to recharge power source 64 as discussed herein. Further, in some example, IMD 12 may only utilize a plurality of coils 14 as discussed herein (e.g., coils that may be coupled in series and series opposition in response to a detected parameter) for one of either telemetry or recharging functions. Put differently, in some examples, IMD 12 may include a single coil (e.g., that is not configured to be coupled in series opposition with another coil) to provide telemetry or recharging functions.

In general, IMD 12 may comprise any suitable arrangement of hardware, alone or in combination with software and/or firmware, to perform the various techniques described herein attributed to IMD 12 and processing circuit 52. In various examples, processing circuit 52 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Memory 62 may include random-access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Memory 62 may store stimulation programs, sense or stimulation electrode combinations, or other instructions that specify therapy parameter values for the therapy provided by stimulation circuit 50 and IMD 12. Moreover, although processing circuit 52, stimulation circuit 50, and telemetry circuit 54 are described as separate portions of circuitry, in some examples processing circuit 52, stimulation circuit 50, and/or telemetry circuit 54 may be fully or partially integrated with each other. In some examples, processing circuit 52, stimulation circuit 50, and/or telemetry circuit 54 correspond to individual hardware units, such as ASICs, DSPs, FPGAs, or other hardware units. Similarly, though switches 56 and sensors 58 are depicted as separate components, in other examples switches 56 and sensors 58 may be integrated into or be coupled directly to (in the case of sensors 58) one or more of processing circuit 52, stimulation circuit 50, and telemetry circuit 54. In some examples, many components of FIG. 2, such as processing circuit 52, stimulation circuit 50, telemetry circuit 54, and memory 62, may be hermetically sealed within a housing of IMD 12.

Stimulation circuit 50 may generate and deliver electrical stimulation under the control of processing circuit 52. In some examples, processing circuit 52 controls stimulation circuit 50 by accessing memory 62 to selectively access and load at least one of the stimulation programs to stimulation circuit 50. For example, in operation, processing circuit 52 may access memory 62 to load one of the stimulation programs to stimulation circuit 50. In such examples, relevant stimulation parameters may include a voltage amplitude, a current amplitude, a pulse rate, a pulse width, a duty cycle, or the combination of electrodes 22. Processing circuit 52 may use these stimulation parameters to cause stimulation circuit 50 to deliver the electrical stimulation signal. Although stimulation circuit 50 may be configured to generate and deliver electrical stimulation therapy via one or more of electrodes 22 of lead 20, stimulation circuit 50 may be configured to provide different therapy to patient 16. For example, stimulation circuit 50 may be configured to deliver, e.g., configured with a pump to provide, drug delivery therapy via a catheter. These and other therapies may be provided by IMD 12.

Processing circuit 52 and telemetry circuit 54 may control the exchange of information with external devices such as charging device 28 and/or external programmer 30 (though, as discussed herein, in some examples charging device 28 and programmer 30 may be integrated together into a single device). Telemetry circuit 54 may be configured for wireless communication, e.g., using radio frequency protocols or inductive communication protocols. Telemetry circuit 54 may use coils 14A to communicate with programmer 30, for example. Processing circuit 52 may transmit operational information to and receive stimulation programs or therapy parameter adjustments from programmer 30 via coils 14A and telemetry circuit 54. Also, in some examples, IMD 12 may communicate with other implanted devices, such as stimulators, control devices, or sensors, via coils 14A and telemetry circuit 54. Examples of local wireless communication techniques that may be employed to facilitate communication between an external device and IMD 12 include RF communication according to the 802.11 or Bluetooth specification sets or other standard or proprietary telemetry protocols.

Though coils 14A are depicted as a single entity for purposes of illustration, it is to be understood that coils 14A represents two or more individual coils that may be coupled together and to telemetry circuit 54 as described herein. Coils 14A may include two or more coils of wire that are wrapped around or within IMD 12, or printed traces or the like that are capable of inductive communication protocols. Coils 14A may be configured to transmit or receive a signal using the communication techniques described above. Telemetry circuit 54 may cause coils 14A to create and transmit a signal (e.g., transmit a signal to charging device 28 and/or programmer 30). Further, a signal received by coils 14A (e.g., as sent by charging device 28 and/or programmer 30) may be managed by telemetry circuit 54. Processing circuit 52 and/or telemetry circuit 54 may cause switching circuitry 56A to couple coils 14A in series to cause coils 14A to receive or transmit signals, though processing circuit 52 is described herein as controlling coupling of coils 14A for purposes of clarity. When switching circuitry 56A couples all coils 14A in series, all coils 14A may be functionally wound or coiled (both words used interchangeably herein) in a same direction with a current (e.g., a current from telemetry circuit as generated using power source 64) induced in the same direction through all coils 14A by an external field.

IMD 12 may include sensor 58A, which may be a measurement circuit configured to measure the current and/or voltage induced during inductive electromagnetic coupling. Processing circuit 52 may use sensor 58A to determine when an induced current surpasses a threshold. In some examples, the transmitted power may be used to approximate the temperature of IMD 12 and that of the surrounding tissue. This method may be used to indirectly measure the temperature of tissue in contact with the housing of IMD 12. Alternatively, sensor 58A may be a temperature sensor that includes one or more components (e.g., thermocouples or thermistors) configured to measure the temperature of IMD 12. Temperature sensor 58A may be disposed internal of the housing of IMD 12, contacting the housing of IMD 12, formed as a part of the housing of IMD 12, or disposed external of the housing of IMD 12. As described herein, temperature sensor 58B may be used to directly measure the temperature of IMD 12 and/or tissue surrounding and/or contacting the housing of IMD 12. While in some examples temperature sensor 58A may contact a housing of IMD 12, in other examples temperature sensor 58A may contact coils 14A, or both, or neither. For example, temperature sensor 58A may be an infrared temperature sensor that is mounted on a circuit board of IMD 12 as a method of measuring temperature of the housing of IMD 12 and/or the tissue surrounding IMD 12 without contacting either the housing and/or tissue. Although a single temperature sensor may be adequate, multiple temperature sensors may provide a better temperature gradient or average temperature of IMD 12. Although processing circuit 52 may continually measure temperature using sensor 58B processing circuit 52 may conserve energy by only measuring temperature during recharge sessions. Further, temperature may be sampled at a rate necessary to calculate the cumulative thermal dose, but the sampling rate may be reduced to conserve power as appropriate.

Processing circuit 52 may modify a coupling of coils 14A using switching circuitry 56A in response to detected parameters from sensor 58A. For example, processing circuit 52 may cause switching circuitry 56A to couple coils 14A in series opposition in response to detecting that a current or temperature as identified using sensor 58A surpasses a threshold. The threshold may be a predetermined threshold saved in memory 62. The threshold may be a point at which IMD 12 and/or patient 16 may experience adverse effects, or a point that is a safety margin below the point at which the IMD 12 and/or patient may experience adverse effects. For example, the adverse effect point may include a temperature of IMD 12 at which patient 16 may experience some discomfort or components of IMD 12 operate with less efficiency.

Coupling coils 14A in series opposition may include coupling coils 14A such that a current that is induced by some of coils 14A may cancel or reduce a current that is reduce a current that is induced by the remainder of coils 14A. For example, all coils 14A may be wound or coiled in a same direction as mounted on IMD 12, but switching circuitry 56A may couple a relative input terminus of one of coils 14A to a relative output terminus of another of coils 14A to effectively cause some of coils 14A to be wound or coiled in an opposing direction to other coils 14A as experienced by a current or signal of IMD 12.

As noted above, IMD 12 may include power source 64. Power source 64 may include one or more capacitors, batteries, or other energy storage devices. Power source 64 may then deliver operating power to the components of IMD 12. Power source 64 may be configured to operate through hundreds or thousands of discharge and recharge cycles. Power source 64 may also be configured to provide operational power to IMD 12 during the recharge process. In some examples, power source 64 may be constructed with materials to reduce the amount of heat generated during charging. In other examples, IMD 12 may be constructed of materials that may help dissipate generated heat at power source 64 and/or recharge coils 14B over a larger surface area of the housing of IMD 12.

Power source 64 may be rechargeable through the use of coils 14B. Coils 14B, which may include two or more coils, may be capable of inductive coupling with a primary coil (e.g., within charging device 28) that is disposed external to patient 16. The induced electrical current may then be used to recharge power source 64. In this manner, the electrical current may be induced in coils 14B and provided to power source 64. The induction may be caused by electrical current generated in the primary coil of external charging device 28. Though recharge coils 14B are depicted in FIG. 2 as a discrete component in relation to telemetry coils 14A, in other examples some or all of recharge coils 14B may be used as telemetry coils 14A.

To recharge power source 64, processing circuit 52 may cause switching circuitry 56B to couple all coils 14B in series, such that all coils 14B are wound or coiled in the same direction and the induced current of each of the coils 14B is substantially summed together before being used to recharge power source 64. In some examples, the induced current may be based on the selected power level (e.g., as selected by a user operating charging device 28). The coupling between coils 14B and the external charging coil may be dependent upon the alignment of coils 14B and the external primary coil in charging device 28. In some examples, the coupling efficiency increases when all coils share a common axis and are in close proximity to each other. The external charging device 28 and/or IMD 12 may provide one or more audible tones or visual indications of the alignment.

Alternatively, in some examples, IMD 12 may not include power source 64, but rather the power required to provide the functionality of IMD 12 may be delivered by an induced current of coils 14B. Put differently, the current induced by coils 14B in response to an electromagnetic field may be routed to components (e.g., processing circuit 52, telemetry circuit 54, stimulation circuit 50) of IMD 12 for pseudo-immediate use, such IMD 12 does not include a component that is configured to store a charge for later use. A device that is external to IMD 12 (e.g., charging device 28) may need to provide the charging electromagnetic signal for the entirety of the duration for which IMD 12 will provide stimulation or monitoring functionality in order for coils 14B to induce a sufficient amount of current for IMD 12 to provide this stimulation or monitoring functionality. In this example, processing circuit 52 may cause switching circuitry 56B to couple coils 14B in series throughout this duration, so that coils 14B may provide a consistent source of power to IMD 12.

As discussed herein, processing circuit 52 may cause switching circuitry 56B to couple coils 14B in series opposition to each other, such that some of coils 14B are functionally wound or coiled in opposing directions and the induced current of these coils 14B are, at least in part, cancelled out. Processing circuit 52 may cause switching circuitry 56B to couple coils 14B in series opposition in response to detecting that an induced current of coils 14B surpasses a threshold. For example, patient 16 may undergo magnetic resonance imagining (MRI) testing, and the resulting electromagnetic fields may cause coils 14B to induce a relatively large current that surpasses the threshold (e.g., while coils 14B are coupled in series). Processing circuit 52 may detect that the induced current surpasses the threshold, in response to which processing circuit 52 may couple coils 14B in series opposition. As a result of being coupled in series opposition, coils 14B may functionally induce little or no current.

IMD 12 may include one or more circuits that filter and/or transform the electrical signal induced in coils 14B to an electrical signal capable of recharging power source 64. For example, in alternating current induction, IMD 12 may include a half-wave rectifier circuit and/or a full-wave rectifier circuit configured to convert alternating current from the induction to a direct current for power source 64. The full-wave rectifier circuit may be more efficient at converting the induced energy for power source 64. However, a half-wave rectifier circuit may be used to store energy in power source 64 at a slower rate. In some examples, IMD 12 may include both a full-wave rectifier circuit and a half-wave rectifier circuit such that IMD 12 may switch between each circuit to control the charging rate of power source 64 and temperature of IMD 12.

Although power source 64 and recharge coils 14B are shown as contained within a main housing of IMD 12, at least one of these components may be disposed outside of the main housing of IMD 12. For example, recharge coils 14B may be disposed outside of the main housing of IMD 12 (e.g., in an overmolding of the house) to facilitate better coupling between recharge coil 14B and a charging coil of external charging device 28. Alternatively, power source 64 and/or recharge coils 70 may be located in a separate housing or a separate component of the same housing of IMD 12. Locating coils 14B outside of a main housing of IMD 12 may improve an ability of coils 14B to receive signals without being attenuated by materials of the main housing (e.g., where the housing is partially or entirely metallic or some other material that blocks electromagnetic fields). Further, in some examples, locating recharge coils 14B relatively further away from the main housing of IMD 12 may increase the available bandwidth of frequencies with which power source 64 may be recharged.

FIGS. 3A and 3B are conceptual and schematic diagrams of coils 114A, 114B (collectively "coils 114") being coupled in series and series opposition, respectively. Coils 114 may be substantially similar to coils 14 as described herein, with the exception of any differences described herein. The conceptual and schematic diagram of FIGS. 3A and 3B include a portion of switching circuitry 156, which may be substantially similar to switching circuitry 56 with the exception of any differences described herein. Switching circuitry 156 may alter a manner in which both coils 114 are coupled relative to terminals 110A, 110B (collectively, "terminals 110") that are coupled to other components and/or circuitry of IMD 12 (e.g., terminals 110 may be coupled to one or more of power source 64, processing circuit 52, or telemetry circuit 54 of FIG. 2). Coils 114 are discussed as if they were mounted on or within IMD 12, though it is to be understood that coils 114 may be mounted on other IMDs in other examples.

Coil 114A may be substantially similar to coil 114B, such that first current 116 that is induced by coil 114A may be substantially similar to second current 118 that is induced by coil 114B when both coils 114 are exposed to substantially similar electromagnetic fields and oriented in a substantially similar fashion. For example, both coils 114 may have a substantially similar (e.g., functionally equal) physical dimensions, such as a substantially similar number of turns, winding radius, pitch, spacing (e.g., between loops), or the like. As used herein, substantially similar components include components that are designed and/or manufactured to be identical in purpose and/or dimensions, though as manufactured the components may be slightly different (e.g., as a result of natural manufacturing imperfections). Further, coil 114A may be wound or coiled in first direction 102 as mounted on IMD 12 and coil 114B may be wound or coiled in second direction 104 as mounted on IMD 12, where first direction 102 and second direction 104 are substantially similar.

Coil 114A may have coil input 106A and coil output 108A, and coil 114B may have coil input 106B and coil output 108B. It is to be understood that inputs 106A, 106B (collectively, "inputs 106") are not intended to imply a point at which signals or current always or typically flows to the respective coils 114 to other components of IMD 12, much like outputs 108A, 108B (collectively "outputs 108") are not intended to imply a point at which signals or current always or typically flows out from the respective coils 114 to other components of IMD 12. Rather, inputs 106 and outputs 108 are used herein to indicate respective terminal points of coils 114 relative to the global winding direction of coils, such that if a respective input 106 of a respective coil 114 is coupled to a respective other output 108 of a respective other coil 114, a potential induced current of the two coils 114 is added together across the IMD 12.

Processing circuit 52 may cause switching circuitry 156 of IMD 12 to electrically couple coils 114 together in series to send a signal or induce a current to recharge power source 64. For example, switching circuitry 156 may couple terminal 110B to input 106B of coil 114B, couple output 108B of coil 114B to input 106A of coil 114A, and coupled output 108A to terminal 110A, such that both coils 114 are coupled in series. As a result of coils 114 being coupled by switching circuitry 156 in series (e.g., as caused by processing circuit 52), coils 114 may "work together" to induce a current to transmit a signal. For example, coils 114 may be telemetry coils (e.g., coils 14A of FIG. 2), and telemetry circuit 54 may cause coils 114 to transmit a signal to an external device such as charging device 28 or programmer 30. In some examples, a combined capacity of both coils 114 may be greater than or equal to a capacity required to receive or transmit a signal, where a capacity of coils 114 may be a surface area of coils 114, or a number of turns and radius of coils 114, or the like. Put differently, IMD 12 may be configured such that a combined capacity of both coils 114 is sufficient to transmit or receive a signal over a desired operational distance, while a single capacity of just one of coils 114 may be insufficient. As such, as a result of switching circuitry 156 of IMD 12 coupling coils 114 in series, coils 114 may be configured to transmit a signal (e.g., a signal as created by telemetry circuit 54 and routed to input 106B or output 108A) through the combined capability of both coils 114.

Conversely, coils 114 may be charging coils (e.g., coils 14A of FIG. 2), such that current that is induced by coils 114 is routed to power source 64 of IMD 12. Where coils 114 are charging coils, processing circuit 52 may cause switching circuitry 156 to couple coils 114 in series (e.g., by coupling input 106A of coil 114A to output 108B of coil 114B, or by coupling input 106B of coil 114B to output 108A of coil 114A) to add together a capacity of both coils 114.

Processing circuit 52 may detect that coils 114 are inducing a current that is above a threshold current. Processing circuit 52 and/or switching circuitry 156 may detect that coils 114 are inducing more than a threshold current using sensor 58. For example, as described herein, sensor 58 may detect temperature (e.g., and therein detect that an induced current has a magnitude that is sufficient to raise a temperature of the IMD 12 or surrounding tissue to above a threshold mount), or sensor 58 may directly detect an induced current.

In response to detecting that an induced current is above a threshold current, switching circuitry 156 may couple coils 114 in series opposition. For example, as depicted in FIG. 3B, switching circuitry 156 may couple terminal 110B to output 108B of coil 114B, couple input 106B of coil 114B to input 106A of coil 114A, and couple output 108A to terminal 110A. As a result of this coupling, first current 116 that is induced by coil 114A (e.g., as a result of an electromagnetic field created by charging device 28 may be substantially negated or cancelled by second current 118 induced by coil 114B as a result of first current 116 of coil 114A being routed to oppose second current 118 of coil 114B as depicted in FIG. 3B. In some examples, processing circuit 52 may cause switching circuitry 156 to couple coils 114 in series opposition until sensor 58 detects that a current (e.g., first current 116 or second current 118) or temperature has dropped below a second threshold, in response to which processing circuit 52 may cause switching circuitry 156 to couple coils 114 in series. The second threshold may be the same as or different than the first threshold. For example, the first threshold at which processing circuit 52 causes switching circuitry 156 to couple coils 114 in series opposition may be a first temperature, and the second threshold at which processing circuit 52 causes switching circuitry 156 to couple coils 114 in series may be a second temperature that is relatively lower than the first temperature. Configuring the processing circuit 52 to cause switching circuitry 156 to couple coils 114 in series subsequent to coupling coils 114 in series opposition at a second threshold that is relatively less than a first threshold may increase an ability of IMD 12 to regulate a temperature and current of IMD 12.

In other examples, whenever processing circuit 52 uses sensor 58 to detect that one or both coils 114 have induced a current that surpasses the first threshold, processing circuit 52 may cause switching circuitry 156 to couple coils 114 in series opposition for a predetermined duration of time. For example, in response to determining that one or both coils 114 may have induced a current that surpasses a threshold, processing circuit 52 may cause switching circuitry 156 to couple coils 114 in series opposition for the subsequent 15 minutes, or hour, or other duration. In some examples, processing circuit 52 may determine a duration for which coils 114 are coupled in series opposition based on a rate at which the induced current approaches and surpasses the threshold (e.g., as determined by processing circuit 52), where a relatively faster approach/steeper rate towards the threshold (e.g., where one or both coils 114 induced a current that surpassed the threshold temperature in a relatively short period of time) results in a relatively longer duration for which coils 114 are coupled in series opposition.

In some examples, one coil 114 may have a relatively greater capacity than the other coil 114. For example, coil 114A may have one more turn than coil 114B. Configuring one coil 114A to be greater than the other coil 114B may enable the combination of coils 114 to still induce a current or transmit or receive a signal when coils 114 are coupled in series opposition, albeit at a relatively lower capacity. For example, coils 114 may be recharging power source 64, but coils 114 may induce too large of a current that raises a temperature of IMD 12 past the first threshold, such that processing circuit causes switching circuitry 156 to couple coils 114 in series opposition for the subsequent two minutes (e.g., as a result of the relatively low rate at which the induced current of coils 114 caused the temperature of IMD 12 to rise). Where coil 114A has a greater capacity than coil 114B (e.g., a 10% greater capacity as a result of an additional turn made by coil 114A relative to coil 114B), coils 114 may still induce a current that may cause power source 64 to charge as IMD 12 cools down. Similarly, coils 114 may be telemetry coils 114 implanted in patient, and coils 114 may induce a current that surpasses a threshold as a result of patient 16 undergoing an MRI. In this example, processing circuit 52 may cause switching circuitry 156 to couple coils 114 in series opposition, and as a result of the relatively greater capacity of coil 114A IMD 12 may still receive and transmit signals (e.g., though potentially with a relatively reduced operational range).

FIGS. 4A and 4B are conceptual and schematic diagrams of coils 214A, 214B, 214C (collectively "coils 214") being coupled in series and series opposition, respectively. Coils 214 may be substantially similar to coils 14 and coils 114 as described herein, with the exception of any differences described below. The conceptual and schematic diagram of FIGS. 4A and 4B include a portion of switching circuitry 256, which may be substantially similar to switching circuitry 56 and switching circuitry 156 with the exception of any differences described herein. Switching circuitry 256 may alter a manner in which both coils 214 are coupled relative to terminals 212A, 212B (collectively, "terminals 212") that are coupled to other components and/or circuitry of IMB 12 (e.g., terminals 212 may be coupled to one or more of power source 64, processing circuit 52, or telemetry circuit 54 of FIG. 2). Coils 214 are discussed as if they were integrated into IMB 12, though it is to be understood that coils 214 used in other IMDs in other examples.

Coil 214A may be substantially similar to coil 214B, such that coil 214A may induce first current 216 that is substantially similar to second current 218 induced by coil 214B when uniformly exposed to an electromagnetic field, wherein uniformly exposed includes both coils 214A, 214B being oriented in a substantially similar direction such that a magnitude and direction of the electromagnetic field is substantially equal to both coils 214. However, coil 214C may have a substantially smaller capacity (e.g., as a result of a relatively smaller radius or relatively less turns of coil 214C) than coils 214A, 214B, such that coil 214C may induce a substantially smaller third current 220 as coils 214A, 214B when exposed to the electromagnetic field. Coil 214A may be wound or coiled in first direction 202 as mounted on IMD 12, coil 214B may be physically wound/coiled in second direction 204 as mounted on IMD 12, and coil 214C may be wound/coiled direction in a third direction 210 as mounted on IMD 12, where first direction 202, second direction 204, and third direction 210 are substantially similar.

Coil 214A may have coil input 206A and coil output 208A, coil 214B may have coil input 206B and coil output 208B, and coil 214C may have coil input 206C and coil output 208C. It is to be understood that inputs 206A, 206B, 206C (collectively, "inputs 206") are not intended to imply a point at which signals or current flows to the respective coils 214 from other components of IMD 12, much like outputs 208A, 208B, 208C (collectively "outputs 208") are not intended to imply a point at which signals or current flows out from the respective coils 114 to other components of IMD 12. Rather, inputs 206 and outputs 208 are used herein to indicate respective terminal points of coils 214 relative to the global winding direction of coils, such that if a respective input 206 of a respective coil 214 is coupled to a respective other output 208 of a respective other coil 214, a potential induced current of the two coils 214 is added together.

Processing circuit 52 may cause switching circuitry 256 to couple coils 214 in series to send a signal or induce a current. For example, processing circuit 52 may cause switching circuitry 256 to couple terminal 212B to input 206C of coil 214C, couple output 208C of coil 214C to input 206B of coil 214B, couple output 208B of coil 214B to input 206A of coil 114A, and couple output 208A of coil 214A to terminal 212A, such that all coils 114 are coupled in series. As a result of all coils 214 being coupled in series, all coils 214 may function as a single coil wound or coiled in a single direction to induce a current or to transmit or receive a signal.

Processing circuit 52 and/or switching circuitry 256 may detect that one or more coils 214 are inducing a current that is above a threshold current as described herein. In response to detecting that an induced current is above a threshold current, switching circuitry 256 may couple some of coils 214 in series opposition. For example, as depicted in FIG. 4B, switching circuitry 256 may couple input 206C of coil 214C to input 206A of coil 214A. As a result of this coupling, first current 216 induced by coil 214A (e.g., as a result of an electromagnetic field created by charging device 28) may be substantially negated or cancelled by second current 218 induced by coil 214B that is routed to substantially oppose first current 216, leaving only third current 220 induced by coil 214C.

In other examples, there may be more than three coils 214 that have different relative capacities. For example, the combined capacity of coils 214B and coil 214C may be substantially equal to coil 214A, such that processing circuit 52 may couple both coil 214B and coil 214C to be in series opposition to coil 214A in order to effectively cancel out a net induced current across all coils. In this example, coil 214B may have 30% of the capacity of coil 214A, while coil 214C has 20% of the capacity of coil 214A. In this example, processing circuit 52 may effectively ramp up or ramp down an amount of potential induced current that is cancelled by the coupling of coils 214 in response to a detected current or temperature.

For example, processing circuit 52 may couple both coil 214B and coil 214C in series opposition to coil 214A in response to detecting that IMD 12 has rapidly approached and surpassed a threshold temperature when recharging power source 64, such that substantially no current is induced across coils 214. For example, where second current 218 and third current 220 summed to a substantially similar magnitude as first current 216, the coupling of FIG. 4B may result in substantially no current being induced across all coils 214. Once processing circuit 52 detects (e.g., using sensor 58) that IMD 12 has cooled to a second temperature (e.g., that is below the first threshold), processing circuit 52 may cause switching circuitry 256 to couple coil 214C to be in series with coil 214A while coil 214B is in series opposition with both coil 214A and coil 214C. For example, switching circuitry 256 may couple coil 214B to be in series opposition with both coil 214A and coil 214C by coupling terminal 212B with input 206C of coil 214C, coupling output 208C of coil 214C with output 208B of coil 214B, coupling input 206B of coil 214B with input 206A of coil 214A, and coupling output 208A of coil 214A with terminal 212A. Alternatively, switching circuitry 256 may couple coil 214B to be in series opposition with both coil 214A and coil 214C by coupling terminal 212B with input 206C of coil 214C, coupling output 208C of coil 214C with input 206A of coil 214A, coupling output 208A of coil 214A with output 208B of coil 214B, and coupling input 206B of coil 214B with terminal 212A. Other ways of coupling coils 214 together to configure coil 214B to be in series opposition with both coil 214A and coil 214C are also possible.

Using such configurations, 20% of the possible capacity of coils 214 is used to induce current to recharge power source 64. Subsequent to this, processing circuit 52 may detect that IMD has cooled to a third temperature (e.g., that is below the second temperature), in response to which processing circuit 52 may cause coil 214A and coil 214B to be in series while coil 214C is in series opposition with both, such as by coupling coil input 206C of coil 214C to coil input 206B of coil 214B and coupling coil output 208B of coil 214B to coil input 206A of coil 214A. Other ways of selectively coupling coils 214 are possible to achieve this result.

According to such a configuration, 30% of the capacity of coils 214 is used to induce current to recharge power source 64. Subsequent to this, processing circuit 52 may detect that IMD has cooled to a fourth temperature (e.g., that is below the third temperature) in response to which all coils 214 are coupled in series such that substantially all of the capacity is used to induce current for recharging power source 64. This may be accomplished, for instance, using a configuration such as shown in FIG. 4A, although other configurations are possible.

Figure 5A:
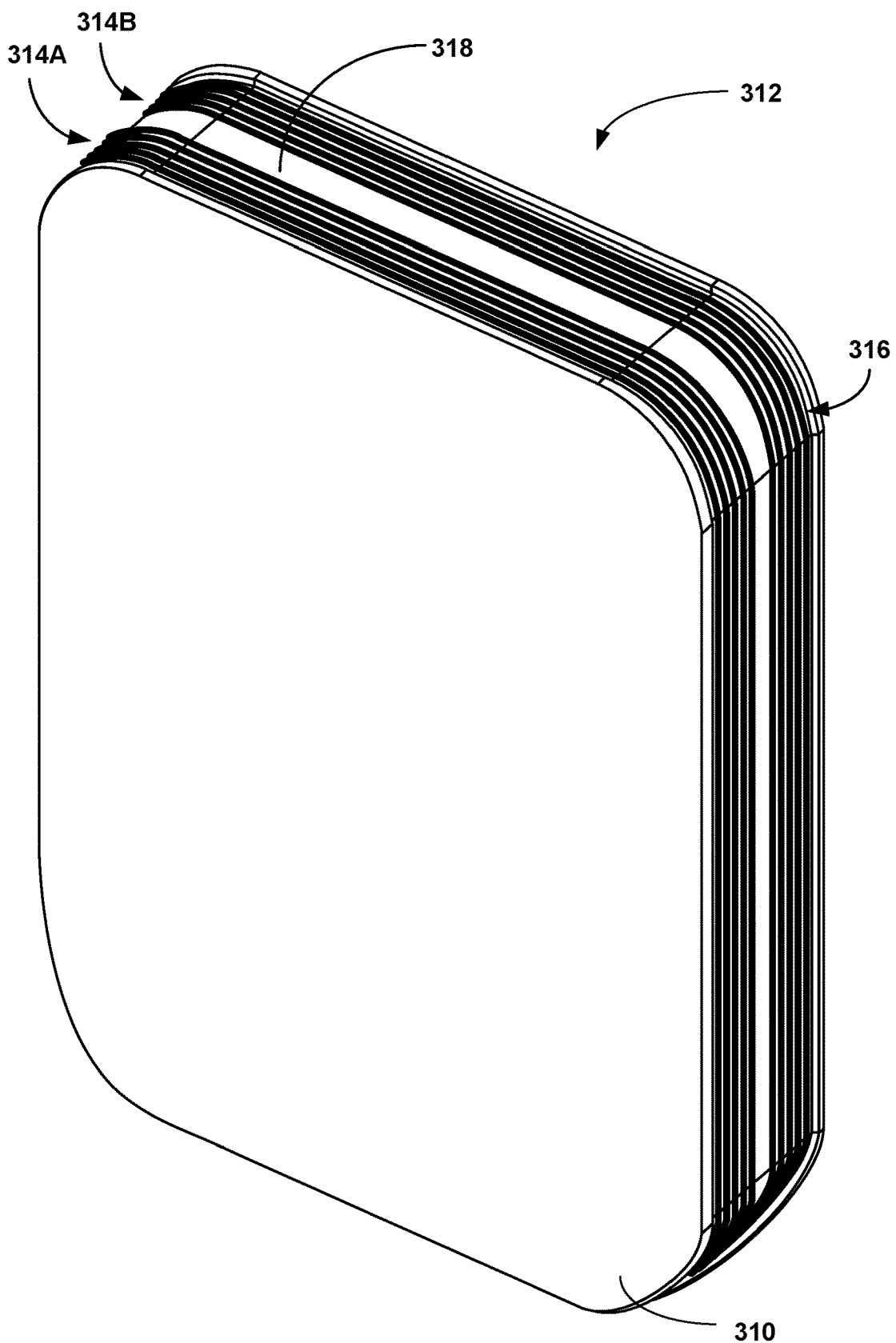
FIGS. 5A-5E are conceptual and perspective views of coils mounted on the housing of an IMD, coils for stacked mounting on a frame, coils for nested mounting on a frame, a coil printed on a surface of an IMD, and two coils of an IMD, respectively.

FIGS. 5A-5E are conceptual and perspective diagrams of example coils. FIG. 5A depicts two coils 314A, 314B (collectively "coils 314") mounted on housing 310 of IMD 312. IMD 312 may be substantially to IMDS 12 of FIGS. 1A and 1B. The general shape of housing 310 is depicted for purposes of illustration only, as housing 310 may be any shape that enables IMD 312 to function as required. For example, in other examples housing 310 may be shaped to include a connection header (e.g., to receive one or more leads 20) that extends from housing 310.

As depicted in FIG. 5A, coils 314 of IMD 312 are secured to outer surface 318 of housing 310 of IMD 312. In certain examples, housing 310 may be partially or entirely metallic, such that housing 310 may have an ability to block some or all electromagnetic fields and/or signals that are created by or intended for coils 314. In such examples, it may be advantageous to secure coils 314 to outer surface 318 of housing 310, such that these coils 314 have an unobstructed path within which electromagnetic fields may be received or transmitted.

Coils 314 may be secured within a recess 316 of housing 310. Recess 316 may extend into housing 310 along a perimeter of housing 310. Recess 316 may have a depth that is greater than a cross-sectional width of coils 360. In some examples, an overmold may cover coils 314 and housing 310 once coils 314 are secured to housing 310. The overmolding may serve to encapsulate the housing 310 and coils 314 and reduce or eliminate sharp corners or edges of housing 310 or coils 314 that may tear or otherwise irritate tissue adjacent IMD 312 once IMD 312 is implanted into patient 16.

Figure 5B:
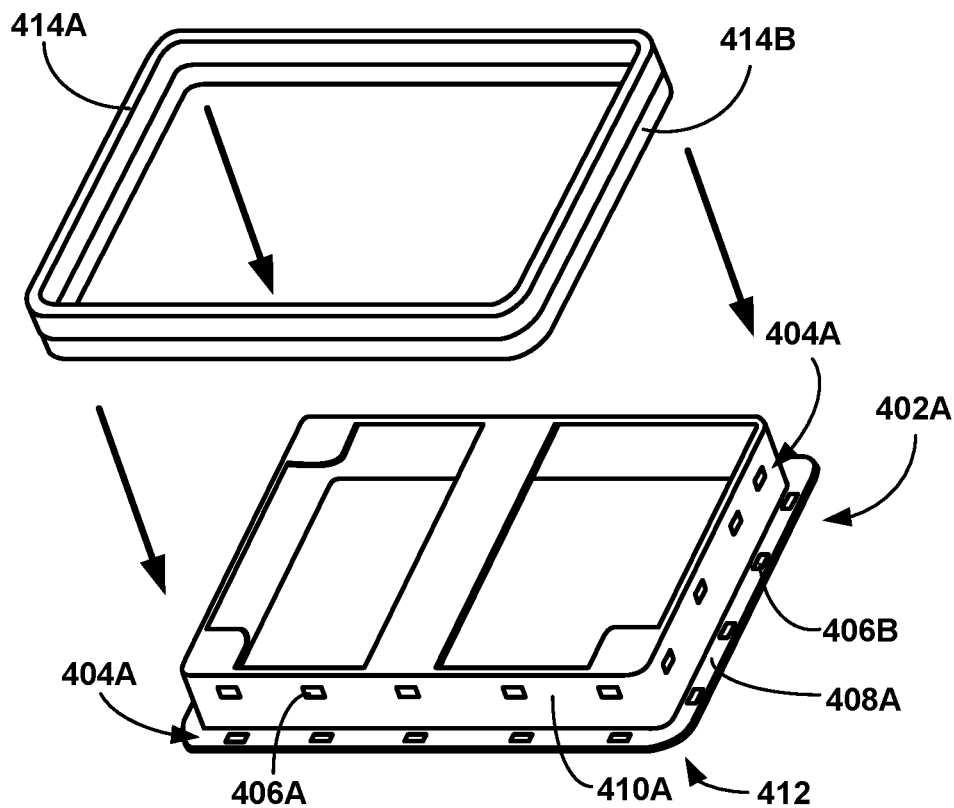
Figure 5C:
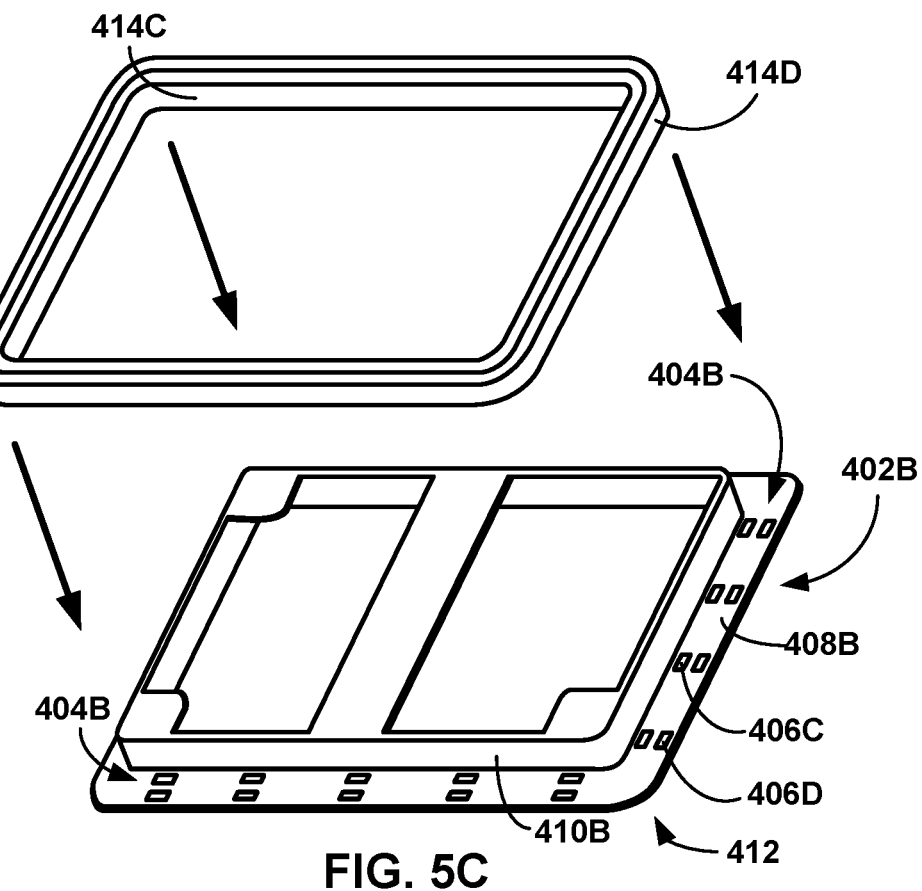

FIGS. 5B and 5C illustrate two conceptual and schematic diagrams of coils 414A-414D (collectively "coils 414") that can be placed on respective frames 402A and 402B (collectively "frames 402") of an IMD, such as IMD 12. Though coils 414 are depicted as solid objects (e.g., without individual windings) for purposes of clarity; it is to be understood that coils 414 may include any number of windings in any configuration that may execute the functions described herein. The coils 414 may be substantially similar to coils 14, 114, 214, or 314 as described herein. In certain examples, coils 414 may be directly placed on frames 402, whereas in other examples coils 414 may be placed on frames 402 within individual respective housings.

Frames 402 may include a die stack for an integrated circuit of IMD 12. For example, frames 402 may be a die stack that attaches directly to a printed circuit board (PCB) of IMD 12, where the PCB includes one or more of stimulation circuit 50, processing circuit 52, telemetry circuit 54, memory 62, switching circuitry 56, or sensors 58. In some examples, coils 414 may be stacked on respective frames 402. For example, as depicted in FIG. 5B, coils 414A and 414B may be stacked (rather than coplanar) as they are received by frame 402A. In other examples, coils 414 may be nested and/or coplanar as they are received by respective frames. For example, as depicted in FIG. 5C, inner coil 414C may fit within outer coil 414D as received on frame 402B, such that coils 414 are nested and coplanar as received by frame 402B. Frames 402 may be sized differently to receive coils 414 in a stacked or coplanar configuration. For example, as depicted, frame 402A may be relatively deeper to receive coils 414 in the stacked configuration, and frame 402B may be relatively wider to receive coils 414 in the nested or coplanar configuration.

In some examples, frames 402 may include a plurality of pads 406A-406D (collectively "pads 406") along a respective perimeter 404A, 404B (collectively "perimeters 404") of frame 402. Pads 406 may be metallized or otherwise conductive. Conductive traces that are on or embedded within frame 402 may electrically couple some pads 406 to coils 414 (e.g., as controlled by switching circuitry 56), while other pads 406 of frame 402 be configured to secure frame 402 and/or coils 414 to PCB. For example, where IMD 12 includes two coils 414 (e.g., as in FIGS. 3A and 3B), frame 402 may include two connective metallic pads 406 per coil 414, where two connective pads 406 connect (through conductive traces and switching circuitry) to an input and output of first coil 414A, and two other connective pads 406 connect (through conductive traces and switching circuitry) to an input and output of second coil 414B. Where IMD 12 contains more coils 414, frame 402 may include more respective connective pads 406 to couple to the respective more coils 414.

Pads 406 may be located on lips 408A, 408B (collectively "lips 408") of perimeters 404 and/or pads 406 may be located on walls 410A, 410B (collectively "walls 410") of perimeters 404. Pads 406 along perimeters 404 of frames 402 may be arranged at different locations along lips 408 and walls 410 depending upon the respective configurations of coils 414. For example, where coils 414 are stacked as depicted in FIG. 5B, some pads 406 such as pad 406B may be located along lip 408A of perimeter 404A. On this lip 408A, pads 406 such as pad 406B may secure or electrically couple with a "bottom" coil 414B once stacked coils 414 are received by frame 402A. Similarly, some pads 406 such as pad 406A may be located along wall 410A of perimeter 404A, where these pads 406 such as pad 406A may secure or electrically couple with a "top" coil 414A once stacked coils 414 are received by frame 402A. Alternatively, where coils 414 are nested or coplanar as depicted in FIG. 5C, pads 406 may mostly or exclusively be located on lip 408B on perimeter 404B (e.g., such that no pads 406 are located on wall 410B of perimeter 404B) within two or more rows, with a respective row for each coil 414. In this manner, some pads 406 such as pad 406C may align with an "inner" coil 414C and other pads 406 such as pad 406D may align with an "outer" coil 414D to secure or be electrically coupled with respective coils 414 as described herein.

In some examples, additional pads 406 may be located on bottom surface 412 of frame 402, or the same pads 406 may extend through to bottom surface 412 of frame 402, where bottom surface 412 is a surface of lip 408. From bottom surface 412, pads 406 may connect to adjoining circuitry, such as the circuitry described herein (e.g., processing circuitry, telemetry circuitry, or the like). In this way, coils 414 may be coupled through pads 406 to circuitry that is adjacent to frame 402. By configuring pads 406 to extend through frame 402 to electrically couple coils 414 to respective circuitry, an IMD 12 may reduce or eliminate the need for additional connectors extending through IMD 12.

Figure 5D:
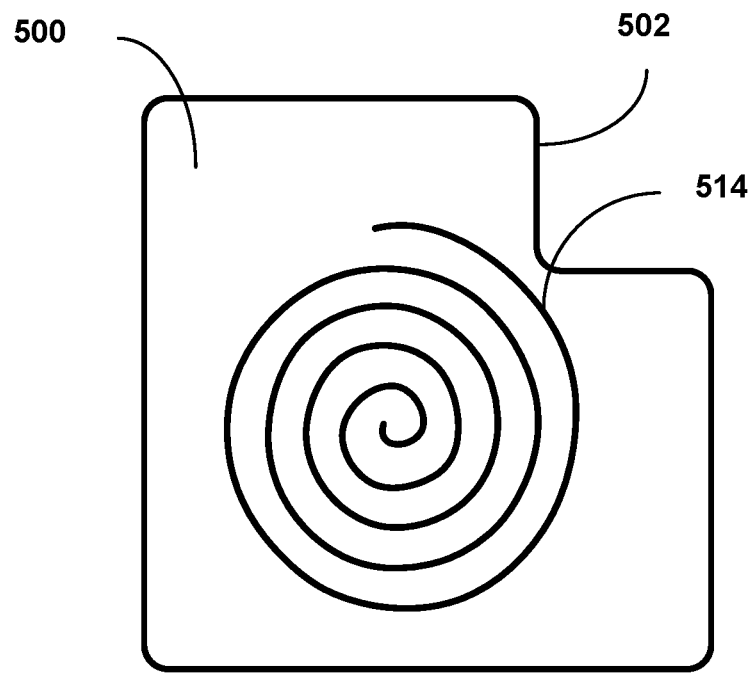

FIG. 5D illustrates a conceptual and schematic diagram of coil 514 that is a printed trace upon surface 500 of component 502 of an IMD, such as IMD 12. Coil 514 may be substantially similar to coils 14, coils 114, coils 214, coils 314, or coils 414 as described herein. Component 502 may be a housing of an IMD, such that surface 500 is an outer surface of the IMD and two or more coils 514 are printed on opposing sides of the housing. In this example, coils 514 may be covered with an overmolding once IMD is assembled and coils 514 are printed on the housing. In other examples, component 502 may be an internal feature of the IMD (e.g., such that component 502 is encapsulated within a housing of the IMD), with different coils 514 printed on different surfaces or all on surface 500 of component 502. In such examples, coils 514 may all be within one plane, or coils 514 may define a 3D structure across planes.

Figure 5E:
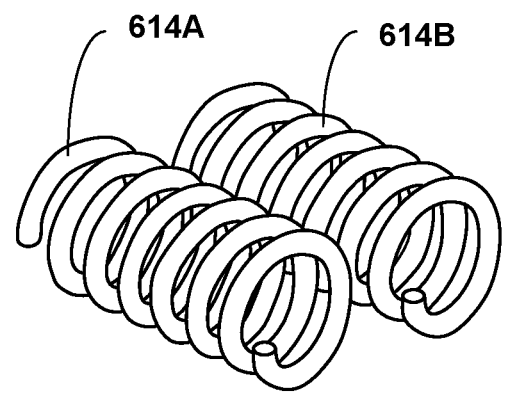

FIG. 5E illustrates a conceptual and schematic diagram of two coils 614A, 614B (collectively "coils 614"). Coils 614 may be substantially similar to coils 14, coils 114, coils 214, coils 314, coils 414, or coils 514 as described herein, with the exception of any differences described below. As depicted, coils 614 may include two helical coils that extend around separate axes. Coils 614 may be located anywhere within a housing of an IMD, or coils 614 may be secured within an overmolding surrounding a housing. In some examples, coils 614 may share a common axis, i.e., be coaxial. In certain examples where coils 614 are coaxial (e.g., as encased within a cable), first coil 614A may be within second coil 614B (e.g., such that first coil 614A has a greater radius than second coil 614B) even as first coil 614A has a substantially equivalent capacity as second coil 614B as a result of first coil 614A having relatively fewer turns than second coil 614B.

Figure 6:
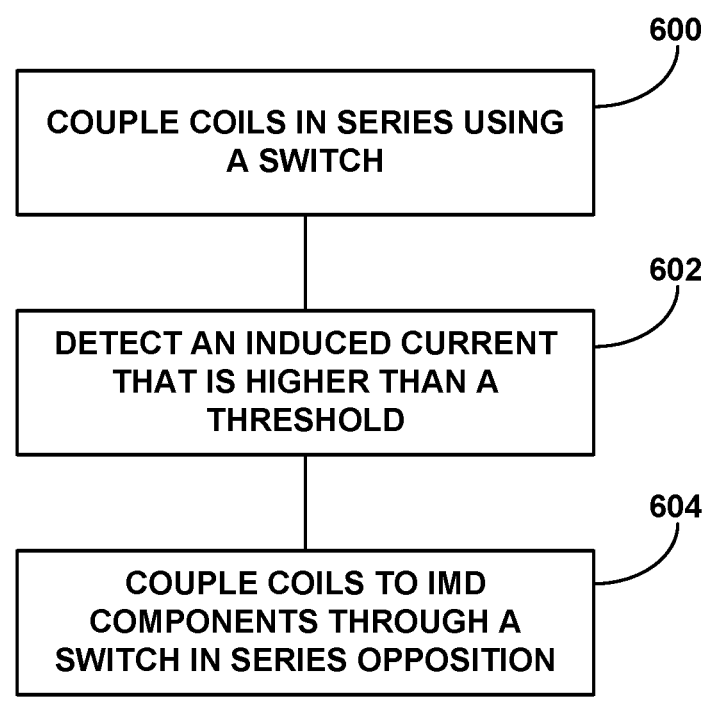
FIG. 6 is a flowchart depicting an example method of coupling two coils in series and series opposition.

FIG. 6 is a flowchart illustrating a method of coupling coils in response to a detected parameter that indicates a magnitude of an induced current of a received signal. FIG. 6 is described predominantly with reference to elements of FIGS. 3A and 3B, with some reference to elements of FIGS. 1-2, though the method of FIG. 6 may be executed with other coils and other IMDs in other examples. Coils 114A and 114B of IMD 12 may be coupled in series (600). Processing circuit 52 may cause switching circuitry 156 to couple coils 114 in series. Coupling coils 114 in series may include coupling coils 114 such that both coils 114 are functionally wound or coiled in a same direction as coupled to components of IMD 12 (e.g., such that currents that are induced by coils 114 will be summed together on IMD 12 rather than cancelling each other out). Processing circuit 52 may cause switching circuitry 156 to couple coils 114 in series so that coils 114 may recharge power source 64 (e.g., with recharge signal) and/or send/receive telemetry signals.

In some examples, processing circuit 52 may cause switching circuitry 156 to couple coils 114 in series whenever processing circuit 52 does not sense a parameter (e.g., a temperature or current) that indicates that coils 114 are inducing a current that is over a threshold. Put differently, processing circuit 52 may cause switching circuitry 156 to couple coils 114 in series as a "default" state, such that processing circuit 52 substantially only temporarily (e.g., for a predetermined period of time or until a predetermined condition is met) causes switching circuitry 156 to couple coils 114 in a configuration other than in series.

Processing circuit 52 may detect that a parameter indicates that a magnitude of an induced current is greater than a threshold (602). Processing circuit 52 may use sensors 58 to determine that the parameter indicates that the magnitude of the induced current is greater than the threshold. For example, the parameter may be a temperature, and sensors 58 may include temperature sensors that are configured to identify temperatures of a portion of IMD 12 or tissue surrounding IMD 12, such that processing circuit 52 is configured to determine that a parameter/temperature indicates that the magnitude of the induced current is greater than a predetermined threshold amount as a result of a rising temperature of IMD 12 and/or surrounding tissue. Alternatively, the parameter may be a current, voltage, or a strength of the electric field, and sensors 58 may include current, voltage, or electric field strength sensors that are configured to pseudo-directly identify a current induced across coils 114.

Processing circuit 52 electrically couples coils 114 in series opposition in response to determining that the parameter indicates that the magnitude of the induced current is higher than a threshold (604). Processing circuit 52 may cause switching circuitry 156 to couple coils 114 in series opposition. Coupling coils 114 in series opposition may include coupling coils 114 to components of IMD 12 such that coils 114 are effectively wound or coiled in opposite directions, such that a current induced over both coils 114 may be effectively cancelled. In some examples, coils 114 are physically disparate, such that first coil 114A has a relatively greater capacity to induce a current than second coil 114B. For example, first coil 114A may have an extra turn or an increased radius or the like in comparison to coil 114B, such that coupling coils 114 in series opposition results in a total induced current that is proportional to the amount that the two coils 114 are physically disparate (e.g., only the additional turn of coil 114A is functionally realized during the process of inducing a current).

Figure 7:
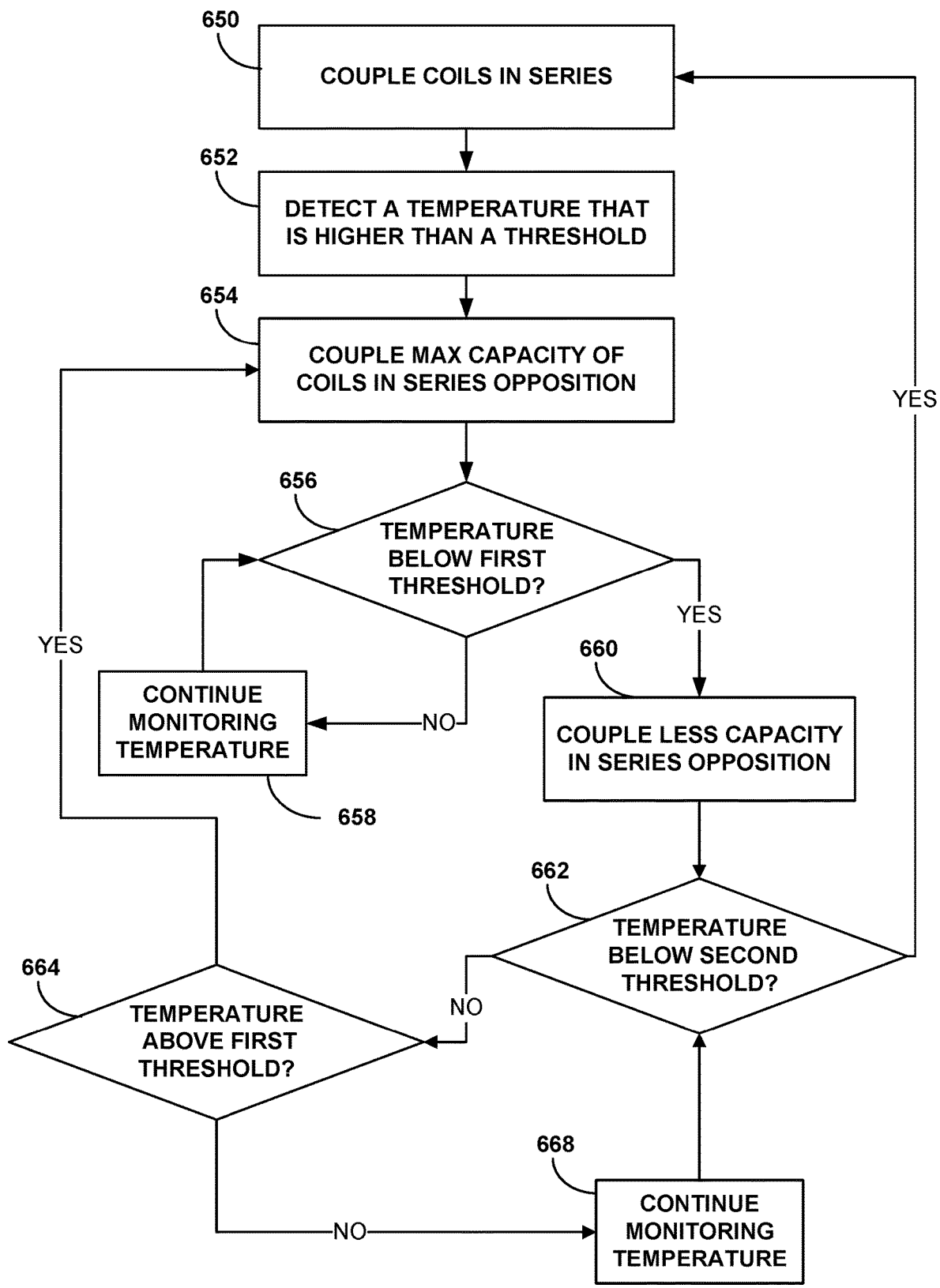
FIG. 7 is a flowchart depicting an example method of coupling three or more coils in series and series opposition.

FIG. 7 is a flowchart illustrating a method of coupling three or more coils in response to a detected magnitude of a received signal. FIG. 7 is described predominantly with reference to FIGS. 4A and 4B, with some reference to FIGS. 1-2, though the method of FIG. 7 may be executed with any of the example coils and IMDs described herein. All coils 214 may be coupled in series (650). As used herein, coils 214 may include first coil 214A of a first capacity, second coil 214B of a second capacity, and third coil 214C of a third capacity, where none of coils 214 have the same capacity yet the sum of the second and third capacity are equal to the first capacity (e.g., coil 214A has 50% of capacity of all coils 214, coil 214B has 35% of the capacity of all coils, and coil 214C has 15% of the capacity of all coils 15%). Processing circuit 52 may cause switching circuitry 256 to couple coils 214 in series. Coupling coils 214 in series may include coupling coils 214 such that all coils 214 are functionally wound or coiled in a same direction as coupled to components of IMD 12 (e.g., such that currents that are induced by coils 214 will be summed together on IMD 12 rather than cancelling each other out).

Processing circuit 52 may detect that a magnitude of an induced current as induced across the three coils 214 is great enough to raise a temperature to above a first threshold (652). Processing circuit 52 may use sensors 58 to determine a magnitude of the induced current. Sensors 58 may include temperature sensors. In other embodiments, a different parameter may be measured to determine current is too large, such as current itself, a voltage across a resistive element, or an electric field strength. Thus, while the following describes use of temperature to trigger reconfiguring coils, it will be understood other types of parameters could be used in addition or as an alternative to temperature. In response to determining that the induced current is higher than a threshold, processing circuit 52 may cause switching circuitry 256 to couple coils 214 in series opposition such that a maximum amount of capacity is internally opposed (654). For example, processing circuit 52 may cause switching circuitry 256 to couple first coil 214A in series opposition with both second coil 214 and third coil 214C, such that an induced current is substantially brought to zero across all coils 214 (e.g., as a result of an induced current of first coil 214A substantially cancelling an induced current of second coil 214B and third coil 214C).

Processing circuit 52 may continue monitoring a temperature or other parameter of IMD 12 and/or surrounding tissues of patient 16 to determine if the temperature or other parameter drops below the first threshold (656). In some examples, processing circuit 52 continue monitoring a temperature of IMD 12 and/or surrounding tissue of patient 16. For example, processing circuit 52 may determine a temperature every few seconds, or every minute, or sensor 58 may be configured to notify processing circuit 52 if the detected temperature. As indicated on FIG. 7, processing circuit 52 may pseudo-continually monitor a temperature of IMD 12 and/or patient 16 tissue until a temperature drops below the first threshold. In some examples, if processing circuit 52 detects that IMD 12 and/or patient 16 tissue has not dropped below the first threshold for a predetermined duration, processing circuit 52 may cause telemetry circuit 54 to send an alarm notification using coils 214 (e.g., by momentarily coupling coils 214 in series to enable an outgoing transmission before recoupling coils 214 in series opposition as in operation 654).

Processing circuit 52 may detect that the temperature of IMD 12 and/or surrounding tissue has dropped below the first threshold, in response to which processing circuit 52 may couple coils 214 such that relatively less capacity of coils 214 is cancelled (660). For example, processing circuit 52 may couple coils 214 such that first and third coil 214A, 214C are in series with each other and second coil 214 is in series opposition, such that, using the example above, 65% of the capacity of coils 214 is inducing a capacity for IMD 12.

In response to coupling coils 214 such that relatively less capacity is cancelled across coils 214, processing circuit 52 may determine whether a detected temperature has dropped below a second threshold (662). The second threshold may be lower than the first threshold, such that the temperature dropping below first the first threshold (656) followed by dropping below the second threshold (662) indicates a continued trend of cooling. If processing circuit 52 determines that the temperature has dropped below the second threshold, processing circuit 52 may couple all coils 214 in series (650). Conversely, if the measured temperature is not below the second temperature, processing circuit 52 may determine whether the measured temperature has raised above the first temperature (664). If the temperature of IMD 12 and/or surrounding tissue has raised above the first temperature, processing circuit 52 may again couple coils 214 in a configuration to block a maximum capacity of coils 214 (654), after which processing circuit 52 may monitor if coils drop below the first temperature (656, 658) as discussed herein. Alternatively, if processing circuit 52 determines that temperature is above the second threshold but below the first threshold, processing circuit 52 may continue monitoring the temperature (668). In this way, processing circuit 52 may be configured to dynamically measure a temperature of IMD 12 and accordingly alter which coils 214 are in series with each other, therein increasing or decreasing an amount of induced current to modulate a capacity of coils 214 while simultaneously regulating a temperature of IMD 12 and/or surrounding tissue of patient 16. Configuring IMD 12 such that processing circuit 52 may dynamically cause switching circuitry 256 to couple coils 214 in series and series opposition and therein increase or decrease an amount of induced current may reduce an amount of stress that is placed on components of IMD 12 and increase an ability to promote the comfort of patient 16 as a result of IMD 12.

It is to be understood that the example method as depicted in FIG. 7 of processing circuit 52 coupling three or more coils 214 in series or series opposition in response to a detected magnitude of a received signal is for purposes of illustration, as in other examples processing circuit 52 may couple three or more coils 214 together in a different manner. For example, processing circuit 52 may couple three or more coils 214 together according to more or less operations than are depicted in FIG. 7, or processing circuit 52 may couple three or more coils 214 together using similar operations as are depicted in FIG. 7 that are executed in a different order.

One example of this may include the response of processing circuit 52 to detecting a temperature that is higher than a threshold (e.g., as at 652). For example, in response to detecting a temperature that is higher than a threshold when coils 214 are coupled in series, processing circuit 52 may initially couple less than the maximum capacity of coils 214 in series opposition. For example, processing circuit 52 may incrementally increase a capacity of the set of coils 214 that is coupled in series opposition as sensors 58 detect that a parameter keeps rising above one or more thresholds, or processing circuit 52 may incrementally increase a capacity that is coupled in series opposition as sensors 58 detect that a parameter remains above one or more thresholds. In this way, as the parameter either continues to rise or otherwise remains above the threshold, processing circuit 52 may couple coils 214 from in-series, to only some coils 214 in-series, to a max capacity of coils 214 in series opposition, or otherwise increase the portion of coils that are coupled in series opposition.

For another example of a different manner in which coils 214 may be coupled in series or series opposition, in some examples processing circuit 52 may use many thresholds that relate to many parameters to modify a coupling of coils 214 (e.g., rather than only using temperature as measured by a temperature sensor as discussed in the example method of FIG. 7). For example, IMD 12 may include multiple sensors 58 that detect multiple parameters of coils 214, such as a first sensor that detects current, a second sensor that detects voltage, and a third sensor that detects temperature. In this example, processing circuit 52 may use detected parameters of each of the first sensor, second sensor, and third sensor when coupling coils 214 in series or series opposition, whether by using different sensors at different times, only altering a coupling of coils 214 in response to two or more of the sensors detecting a value that satisfies a threshold, or the like.

This may include processing circuit 52 modifying a manner in which coils 214 are coupled in response to at least two of the three sensors detecting a parameter that surpasses a respective threshold. For example, processing circuit 52 may be configured to detect but not react to the first sensor sensing that an induced current satisfies a current threshold (e.g., as an induced current may momentarily spike and subsequently drop in a way that does not necessitate any coils 214 being coupled in series opposition). Further, processing circuit 52 may be configured to couple at least some coils 214 in series opposition in response to detecting that the third sensor senses a correlating increase in temperature that satisfies a temperature threshold while the first sensor is still sensing that the induced current satisfies the current threshold (e.g., as, where the first sensor is no longer sensing that the induced current satisfies the current threshold, it is probable that the temperature sensor will sense a corresponding temperature drop below the temperature threshold). In this way, processing circuit 52 may be configured to use multiple sensors 58 to cross-check multiple sensed parameters to verify that the sensed parameter values warrant a response to potentially eliminate "false positives" (e.g., situations where a parameter of IMD 12 temporarily and incorrectly indicates that coupling coils 214 in series opposition reduces a chance of a negative effect, as the negative effect would not have been realized either way).

Alternatively, or additionally, processing circuit 52 may use different parameters as sensed by different sensors 58 in different conditions to couple coils 214 in series or series opposition. For example, some sensors 58 may be more or less accurate in different ranges of their respective parameters, such that processing circuit 52 may use different sensors 58 to determine how to couple coils 214 in response to determining a respective condition of coils 214 (e.g., where the condition may include a temperature, voltage, or current of coils 214, as examples). This may include primarily or exclusively using a sensor when that sensor is within its peak accuracy range. Additionally, or alternatively, this may include never or sparingly using a sensor when that sensor is within a low accuracy range.

This disclosure is primary directed to coupling coils in series or series opposition to alter an amount of current that is induced by the coils when the coils are exposed to an electromagnetic field. However, one or more aspects of this disclosure may also be applicable to generally coupling coils in different configurations to alter an effective coil capacity of an IMD for different applications. For example, aspects of this disclosure may be applicable to effectively increase or decrease an effective operating range of an antenna of an IMD.

Various examples have been described. These and other examples are within the scope of the following claims.

The invention claimed is:

1. An implantable medical device comprising:
   an implantable medical housing;
   a processing circuit within the implantable medical housing;
   a first coil configured to wirelessly receive a signal and secured to the implantable medical device;
   a second coil configured to wirelessly receive the signal and secured to the implantable medical device;
   switching circuitry within the housing, wherein the processing circuit is configured to cause the switching circuitry to selectably couple the first coil to the second coil either in series such that the first coil is coiled in a same direction as a direction in which the second coil is coiled or in series opposition such that the first coil is coiled in an opposite direction as the direction in which the second coil is coiled; and
   a sensor configured to sense a parameter that indicates a magnitude of an induced current that is induced over the first coil and the second coil as a result of receiving the signal, wherein the parameter is at least one of temperature, voltage, or current.

2. The implantable medical device of claim 1, wherein the processing circuit is configured to cause the switching circuitry to selectably couple the first coil to the second coil either in series or in series opposition based on the sensed parameter.

3. The implantable medical device of claim 1, further comprising a power supply for the implantable medical device, wherein the signal is a charging signal, and wherein the first coil and the second coil are configured to provide power from the charging signal to the power supply when the first coil is coupled to the second coil in series.

4. The implantable medical device of claim 1, wherein the first coil has a substantially similar radius and amount of turns as a radius and amount of turns of the second coil, such that when coupled in series opposition the signal received by the first coil is substantially cancelled by the signal received by the second coil.

5. The implantable medical device of claim 1, wherein the first coil and the second coil are coiled coaxially.

6. The implantable medical device of claim 1, wherein the first coil and the second coil are stacked.

7. The implantable medical device of claim 1, wherein the first coil and the second coil are coplanar.

8. The implantable medical device of claim 1, wherein the first coil and the second coil are configured to together send a telemetry signal when coupled in series.

9. The implantable medical device of claim 1, wherein the first coil has at least one of relatively more turns or a relatively greater radius than a number of turns or a radius of the second coil, such that the first coil has a relatively greater capacity to induce current than the second coil when both the first coil and the second coil are uniformly exposed to an electromagnetic field.

10. The implantable medical device of claim 1, further comprising a third coil, wherein:
    the processing circuit is configured to cause the switching circuitry to selectably couple the first coil to the second coil and the third coil either in series such that the first coil is coiled in the same direction as the direction in which the second coil is coiled and a direction in which the third coil is coiled or in series opposition such that the first coil is coiled in an opposite direction as the direction in which the second coil is coiled and the direction in which the third coil is coiled, and
    the processing circuit is configured to cause the switching circuitry to selectably couple the first coil to the second coil and the third coil either in series or in series opposition in response to detected measurements of a parameter that indicates a magnitude of an induced current that is induced over the first coil, the second coil, and the third coil.

11. The implantable medical device of claim 1, wherein the parameter is a temperature of components of the implantable medical device, wherein the processing circuit is configured to cause the switching circuitry to couple the first coil to the second coil in series opposition in response to the detected temperature rising above a threshold temperature.

12. The implantable medical device of claim 1, wherein the parameter is a current measured across at least one of the first coil or the second coil, wherein the processing circuit is configured to cause the switching circuitry to couple the first coil to the second coil in series opposition in response to the detected current rising above a threshold current.

13. A method of managing coils of an implantable medical device comprising:
    coupling, by switching circuitry of the implantable medical device as caused by a processing circuit of the implantable medical device, a first coil secured to the implantable medical device to a second coil secured to the implantable medical device in series such that the first coil is coiled in a same direction as a direction in which the second coil is coiled, wherein both the first coil and the second coil are configured to wirelessly receive a signal;

receiving, by both the first coil and the second coil, the signal;

detecting, by the processing circuit, that a parameter that indicates a magnitude of an induced current that is induced over the first coil and the second coil as a result of receiving the signal surpasses a predetermined threshold; and coupling, by the switching circuitry of the implantable medical device as caused by the processing circuit, the first coil and the second coil in series opposition such that the first coil is coiled in an opposite direction as the direction in which the second coil is coiled.

14. The method of claim 13, further comprising detecting, by the processing circuit, that the parameter that indicates the magnitude of the induced current surpasses the predetermined threshold using a sensor configured to measure a combined induced current of the first coil and the second coil.

15. The method of claim 13, further comprising detecting, by the processing circuit, that the parameter that indicates the magnitude of the induced current surpasses the predetermined threshold using one or more thermocouples or thermistors configured to measure a temperature of the implantable medical device upon receiving the signal, wherein the predetermined threshold is a threshold temperature.

16. The method of claim 13, wherein the predetermined threshold is a first predetermined threshold, further comprising:

detecting, by the processing circuit, that the parameter that indicates the magnitude of the induced current drops below a second predetermined threshold; and coupling, by the switching circuitry of the implantable medical device as caused by the processing circuit, the first coil and the second coil in series such that the first coil is coiled in the same direction as the direction in which the second coil is coiled.

17. The method of claim 16, wherein the first predetermined threshold is of a relatively greater magnitude than the second predetermined threshold.

18. The method of claim 13, wherein the implantable medical device includes a third coil that is secured to the implantable medical device and configured to wirelessly receive the signal, wherein coupling the first coil to the second coil in series further comprises coupling the third coil in series with the first coil and the second coil such that such that the first coil is coiled in the same direction as the direction in which the second coil is coiled and a direction in which the third coil is coiled, wherein detecting that the parameter that indicates the magnitude of the induced current surpasses the predetermined threshold further comprises detecting that the parameter that indicates the magnitude of the induced current that is induced over the first coil, the second coil, and the third coil surpasses the predetermined threshold, and wherein coupling the first coil and the second coil in series opposition further comprises coupling the third coil in series opposition with the first coil such that the first coil is coiled in an opposite direction as the direction in which the second coil is coiled and the direction in which the third coil is coiled, such that the received signal is effectively cancelled across the first coil, the second coil, and the third coil.

19. The method of claim 18, wherein the predetermined threshold is a first predetermined threshold, further comprising:

detecting, by the processing circuit, that the parameter that indicates the magnitude of the induced current has fallen to a second predetermined threshold that is less than the first predetermined threshold; and coupling, by the switching circuitry of the implantable medical device as caused by the processing circuit in response to detecting that the parameter that indicates the magnitude of the induced current has fallen to the second predetermined threshold, the second coil in series with the first coil and in series opposition with the third coil, such that a first amount of the received signal is effectively cancelled across the first coil, second coil, and the third coil.

20. The method of claim 19, further comprising:

detecting, by the processing circuit, that the parameter that indicates the magnitude of the induced current has fallen to a third predetermined threshold that is less than the second threshold; and coupling, by the switching circuitry of the implantable medical device as caused by the processing circuit in response to detecting that the parameter that indicates the magnitude of the induced current has fallen to the third threshold, the third coil in series with the first coil and the second coil in series opposition with the first coil and the third coil, such that a second amount of the received signal is effectively cancelled across the first coil, second coil, and the third coil, wherein the second amount is less than the first amount.

21. The method of claim 20, further comprising:

detecting, by the processing circuit, that the parameter that indicates the magnitude of the induced current has fallen to a fourth predetermined threshold that is less than the third threshold; and coupling, by the switching circuitry of the implantable medical device as caused by the processing circuit, the first coil, the second coil and the third coil in series to one another such that substantially none of the received signal is canceled across the first coil, the second coil, and the third coil.

22. An implantable medical device comprising:

an implantable medical housing;

a processing circuit within the implantable medical housing;

one or more leads configured to extend from the implantable medical housing and be implanted into a brain of a patient;

one or more electrodes at a distal end of the one or more leads that are configured to deliver electrical stimulation to the brain of the patient;

a stimulation circuit configured to generate the electrical stimulation;

a power supply configured to provide power for the generation of the electrical stimulation;

switching circuitry that is electrically coupled to the processing circuit;

a first coil that is coupled through the switching circuitry to the power supply and configured to wirelessly receive a charging signal;

a second coil that is coupled through the switching circuitry to the power supply and configured to wirelessly receive the charging signal, wherein the processing circuit is configured to cause the switching circuitry to selectably couple the first coil to the second coil either in series such that the first coil is coiled in a same direction as a direction in which the second coil is coiled or in series opposition such that the first coil is coiled in an opposite direction as the direction in which the second coil is coiled; and a sensor configured to sense a parameter that indicates a magnitude of an induced current that is induced over the first coil and the second coil as a result of receiving the signal, wherein the parameter is at least one of temperature, voltage, or current.

23. The implantable medical device of claim 22, further comprising a third coil, wherein:

the processing circuit is configured to cause the switching circuitry to selectably couple the first coil to the second coil and the third coil either in series such that the first coil is coiled in the same direction as the direction in which the second coil is coiled and a direction in which the third coil is coiled or in series opposition such that the first coil is coiled in an opposite direction as the direction in which the second coil is coiled and the direction in which the third coil is coiled; and the processing circuit is configured to cause the switching circuitry to couple the first coil to the second coil and the third coil either in series or in series opposition in response to detected measurements of a parameter that indicates a magnitude of an induced current that is induced over the first coil, the second coil and the third coil.

* * * * *